(12) United States Patent
Hansen et al.

(10) Patent No.: US 8,489,339 B2
(45) Date of Patent: Jul. 16, 2013

(54) CRYSTALLINE COMPOSITION OF GM-CSF/GM-CSFR

(75) Inventors: Guido Hansen, Luebeck (DE); Timothy Robert Hercus, Clapham (AU); Angel Francisco Lopez, Medindie (AU); William John McKinstry, North Carlton (AU); Michael William Parker, Newport (AU)

(73) Assignees: St. Vincent's Institute of Medical Research (AU); Central Adelaide Local Health Network (AU)

( * ) Notice: Subject to any disclaimer, the term of this patent is extended or adjusted under 35 U.S.C. 154(b) by 294 days.

(21) Appl. No.: 12/513,497

(22) PCT Filed: Nov. 1, 2007

(86) PCT No.: PCT/AU2007/001674
§ 371 (c)(1),
(2), (4) Date: Aug. 26, 2009

(87) PCT Pub. No.: WO2008/052277
PCT Pub. Date: May 8, 2008

(65) Prior Publication Data
US 2011/0150884 A1    Jun. 23, 2011

Related U.S. Application Data

(60) Provisional application No. 60/856,781, filed on Nov. 3, 2006, provisional application No. 60/887,136, filed on Jan. 29, 2007.

(51) Int. Cl.
*G01N 23/02* (2006.01)

(52) U.S. Cl.
USPC .............................. 702/27; 436/86

(58) Field of Classification Search
None
See application file for complete search history.

(56) References Cited

FOREIGN PATENT DOCUMENTS
WO    WO00/47620 A1    8/2000

OTHER PUBLICATIONS

Wiencek, J. M. Ann. Rev. Biomed. Eng. 1999, 1, 505-534.*
Collaborative Computational Project, "The CCP4 Suite: Programs for Protein Crystallography," Acta Crystallogr. D Biol. Crystallogr. 50:760, 1994.
Barry et al, "Two Contiguous Residues in Human Interleukin-2, Aps21 and Clu22, Selectively Interact with the α and β-Chains of Its Receptor and Participate in Function," J. Biol. Chem. 269:8488, 1994.
Carr et al,"Structure of the Complete Extracellular Domain of the Common β Subunit of the Human GM-CSF, IL-3, and IL-5 Receptors Reveals a Novel Dimer Configuration," Cell 104:291-300, 2001.
Carr et al, "An improved resolution structure of the human β common receptor involved in IL-3, IL-5, and GM-CSF signalling which gives better definition of the high-affinity binding epitope," Acta Crystallogr. F62:509-513, 2006.

(Continued)

*Primary Examiner* — Nashaat Nashed
(74) *Attorney, Agent, or Firm* — Knobbe Martens Olson & Bear, LLP

(57) ABSTRACT

The present invention relates generally to the field of crystallography. More particularly, the present invention provides crystalline forms of a complex between granulocyte macrophage-colony stimulating factor (GM-CSF) and its receptor (GM-CSFR). The present invention further provides methods for the design and selection of modulators of GM-CSF/GM-CSFR interaction and signaling as well as signaling of other cytokines.

6 Claims, 15 Drawing Sheets

OTHER PUBLICATIONS

D'Andrea et al, "Extracellular truncations of h beta c, the common signaling subunit for interleukin-3 (IL-3), granulocyte-macrophage colony-stimulating factor (GM-CSF), and IL-5, lead to ligand-independent activation," Blood 87:2641-2648, 1996.

Devos et al, "Recombinant Soluble Human Interleukin-5 (hIL-5) Receptor Molecules," J. Biol. Chem. 268:6581, 1993.

Fleetwood et al, "Functions of Granulocyte-Macrophage Colony-Stimulating Factor," Crit. Rev. Immunol. 25:405, 2005.

Guthridge et al, "Mechanism of Activation of the GM-CSF, IL-3 and IL-5 Family of Receptors" Stem Cells 16:301, 1998.

Guthridge et al, "Growth factor pleiotropy is controlled by a receptor Tyr/Ser motif that acts as a binary switch," EMBO J 25:479-489, 2006.

Hercus et al, "Specific human granulocyte-macrophage colony-stimulating factor antagonists," Proc. Natl. Acad. Sci. USA 91:5838, 1994.

Hercus et al, "Identification of residues in the first and fourth helices of human granulocyte-macrophage colony-stimulating factor involved in biologic activity and in binding to the alpha- and beta-chains of its receptor," Blood 83:3500, 1994.

Huston et al, "Protein engineering of anitbody binding sites: Recover of specific activity in an anti-digoxin single-chain Fv analogue produced in *Escherichia coli*," Proc. Natl. Acad. Sci. USA 85:5879-5883, 1988.

Jenkins et al, "Interacting Residues in the Extracellular Region of the Common β Subunit of the Human Granulocyte-Macrophage Colony-stimulating Factor, Interleukin (IL)-3, and IL-5 Receptors Involved in Constitutive Activation," J. Biol. Chem. 271:29707, 1996.

Jenkins et al, "A Cell Type-specific Constitutive Point Mutant of the common β-Subunit of the Human Granulocyte-Macrophage Colony-stimulating Factor (GM-CSF), Interleukin (IL)-3, and IL-5 Receptors Requires the GM-CSF Receptor α-Subunit for Activation," J. Biol. Chem. 274:8669, 1999.

Kaushansky and Karplus, "Hematopoietic growth factors: understanding functional diversity in structural terms," Blood 82:3229, 1993.

Kitamura et al, "Establishment and Characterization of a Unique Human Cell Line That Proliferates Dependently on GM-CSF, IL-3, or Erythropoietin," J. Cell Physiol. 140:323-34, 1989.

Lia et al, "A Dominant Negative Granulocyte-Macrophage Colony-stimulating Factor Receptor α Chain Reveals the Multimeric Structure of the Receptor Complex," J. Biol. Chem. 271:28287, 1996.

Lock et al, "Histidine-367 of the human common β chain of the receptor is critical for high-affinity binding of human granulocyte-macrophage colony-stimulating factor," Proc. Natl. Acad. Sci. USA 91:252, 1994.

McClure et al, "Molecular assembly of the ternary granulocyte-macrophage colony-stimulating factor receptor complex," Blood 101:1308, 2003.

Mulhern et al, "The solution structure of the cytokine-binding domain of the common beta-chain of the receptors for granulocyte-macrophage colony-stimulating factor, interleukin-3 and interleukin-5," J Mol Biol. 297, 989-1001, (2000).

Murphy et al, "A Novel Functional Epitope Formed by domains 1 and 4 of the Human Common β-Subunit Is Involved in Receptor Activation by Granulocyte Macrophage Colony-stimulating Factor and Interleukin 5," J. Biol. Chem. 278:10572, 2003.

Murphy et al, "Interleukin-3 Binding to the Murine βIL-3 and Human βc Receptors Involves Functional Epitopes Formed by Domains 1 and 4 of different Protein Chains," J. Biol. Chem. 279:26500, 2004.

Murphy and Young, "IL-3, IL-5, and GM-CSF Signaling: Crystal Structure of the Human Beta-Common Receptor," Vitamins and Hormones 74, 1-30 (2006).

Muto et al, "High Affinity Chimeric Human Granulocyte-Macrophage Colony-Stimulating Factor Recerptor Carrying the Cytoplasmic Domain of the β Subunit but not the α Subunit Transduces Growth Promoting Signals in Ba/F3 Cells," Biochem. Biophys. Res. Commun. 208:368, 1995.

Rajotte et al, "Crucial Role of the Residue R280 at the F'-G- Loop of the Human Granulocyte/Macrophage Colony-stimulating Factor Receptor α Chain for Ligand Recognition," J. Exp. Med. 185:1939, 1997.

Rossjohn et al, "Structure of the activation domain of the GM-CSF/IL-3/IL-5 receptor common beta-chain bound to an antagonist," Blood 95:2491, 2000.

Stomski et al, "Human Interleukin-3 (IL-3) Induces Disulfide-Linked IL-3 Receptor α- and β-Chain Heterodimerization, Which Is Required for Receptor Activation but Not High-Affinity Binding," Mol. Cell. Biol. 16:3035-3046, 1996.

Stomski et al, "Identification of a Cys Motif in the common β Chain of the Interleukin 3, Granulocyte-Macrophage Colony-stimulating Factor, and Interleukin 5 Receptors Essential for Disulfide-linked Receptor Heterodimerization and Activition of the All Three Receptors," J. Biol. Chem. 273:1191-1199, 1998.

Sun et al, "Simultaneous Antagonism of Interleukin-5, Granulocyte-Macrophage Colony-Stimulating Factor, and Interleukin-3 Stimulation of Human Eosinophils by Targetting the Common Cytokine Binding Site of Their Receptors," Blood, 94:1943-1951, 1999.

Tavernier et al, "Identification of receptor-binding domains on human interleukin 5 and design of an interleukin 5-dervied receptor antagonist," Proc. Natl. Acad. Sci. USA 92:5194, 1995.

Wells and de Vos, "Hematopoietic Receptor Complexes," Annu. Rev. Biochem. 65:609, 1996.

Woodcock et al, "Three residues in the common β chain of the human GM-CSF, IL-3 and IL-5 receptors are essential for GM-CSF and IL-5 but not IL-3 high affinity binding and interact with Clu21 of GM-CSF," EMBO J. 13:5176, 1994.

Woodcock et al, "A Single Tyrosine Residue in the Membrane-proximal Domain of the Granulocyte-Macrophage Colony-stimulating Factor, Interleukin (IL)-3, and IL-5 Receptor Common β-Chain Is Necessary and Sufficient for High Affinity Binding and Signaling by All Three Ligands," J. Biol. Chem. 271:25999, 1996.

Woodcock et al, "The Human Granulocyte-Macrophage Colony-Stimulating Factor (GM-CSF) Receptor Exists as a Preformed Receptor Complex That Can Be Activated by GM-CSF, Interleukin-3, or Interleukin-5," Blood 90:3005, 1997.

Murphy, J.M. et al. 2003 "A novel functional epitope formed by domains 1 and 4 of the human common β-subunit is involved in receptor activation by Granulocyte Macrophage Colony Stimulating Factor and Interleukin 5" *Journal of Biological Chemistry*, Jan. 12, 2003, vol. 278 Issue 12 : 10572-10577.

Murphy, J.M. et al. 2006 "IL-3, IL-5 and GM-CSF signaling: Crystal structure of the human beta-common receptor" *Vitamins and Hormones*, Oct. 5, 2006, vol. 74: 1-30.

Rossjohn, J. et al. 2000 "Structure of the activation domain of the GM-CSF/IL-3/IL-5 receptor common β-chain bound to an antagonist" *Blood*, Apr. 15, 2000, vol. 95 Issue 8 :2491-2498.

* cited by examiner

A

B

CRYSTALLINE COMPOSITION OF GM-CSF/GM-CSFR

RELATED APPLICATIONS

This application is a U.S. National Phase of International Application No. PCT/AU2007/001674, filed Nov. 1, 2007, designating the U.S. and published in English on May 8, 2008 as WO 2008/052277 A1, which claims the benefit of U.S. provisional application No. 60/856,781, filed Nov. 3, 2006 and U.S. provisional application No. 60/887,136, filed Jan. 29, 2007.

This application incorporates by reference the sequence listing submitted as ASCII text filed via EFS-Web on Mar. 13, 2013. The Sequence Listing is provided as a filed entitled "March Updated ST25 Sequence Listing—DAVI293.003APC", created on Mar. 13, 2013 and which is 17.6 kilobytes in size.

FIELD

The present invention relates generally to the field of crystallography. More particularly, the present invention provides crystalline forms of a complex between granulocyte macrophage-colony stimulating factor (GM-CSF) and its receptor (GM-CSFR). The present invention further provides methods for the design and selection of modulators of GM-CSF/GM-CSFR interaction and signaling as well as signaling of other cytokines.

BACKGROUND

Bibliographic details of references in the subject specification are also listed at the end of the specification.

Reference to any prior art in this specification is not, and should not be taken as, an acknowledgment or any form of suggestion that this prior art forms part of the common general knowledge in any country.

A common feature of cytokine receptor activation is ligand-induced receptor aggregation involving the homo- or hetero-dimerization of two or more receptor components and their assembly into a fully functional signaling complex. Structural data for hetero-dimeric receptor families that utilize a common binding and signaling subunit such as the IL-2 and IL-6 receptor systems have provided unique insights into their functional activation (Wang et al, *Science* 310:1159, 2005; Stauber et al, *Proc. Natl. Acad. Sci. USA* 103:2788, 2006; Boulanger et al, *Science* 300:2101, 2003). The GM-CSF, IL-3, and IL-5 family of receptors remains the last major group of class I hematopoietic receptor systems to be structurally elucidated.

The GM-CSF, IL-3 and IL-5 family of cytokines regulates the survival, proliferation, differentiation and functional activation of hematopoietic cells with GM-CSF also controlling dendritic cell and T cell function, thus bridging innate and acquired immunity (Guthridge et al, *Stem Cells* 16:301, 1998). Accordingly, GM-CSF is used for the expansion of hematopoietic cells after bone marrow transplantation, for the activation of mature cell function in infectious diseases, and as an adjuvant to bolster anti-tumor immunity (Fleetwood et al, *Crit. Rev. Immunol.* 25:405, 2005). Conversely, GM-CSF, IL-3 and IL-5 have all been implicated in multiple pathologies resulting from excessive or aberrant expression of the cytokines or their receptors, in conditions such as arthritis, asthma, autoimmunity and leukaemia (Guthridge et al, supra 1998). Their receptors are expressed at very low level (100-300 per cell) on the surface of hematopoietic cells and comprise a cytokine-specific alpha subunit and a beta subunit (βc) that is common to all three receptors (Guthridge et al, supra 1998). Each alpha subunit binds cytokine with low affinity (0.2 nM to 100 nM) but the presence of βc converts this to high affinity (100 pM) causing dimerization of both subunits and receptor activation. Structure-function studies of GM-CSF, IL-3 and IL-5 and their receptors have noted regions of importance for ligand binding and receptor activation while receptor mutants that can function in a ligand-independent manner have suggested novel activation mechanisms. However, the structural elements and underlying mechanisms that can explain both forms of receptor activation remain elusive.

Activation of the GM-CSF receptor family by ligand-induced receptor dimerization, shows similarities and important differences to the IL-2 and IL-6 systems. First, in the GM-CSF receptor family, the alpha and beta subunits both participate in signaling such that deletion of the alpha chain cytoplasmic domains abolishes receptor function, suggesting an essential membrane proximal interaction of both subunits is required for receptor activation (Lia, *J. Biol. Chem.* 271: 28287, 1996). Secondly, some of the GM-CSF receptor exists as a preformed complex, a finding that explains the rapid association kinetics of GM-CSF and the ability of the GM-CSF receptor to be co-immunoprecipitated with IL-3 and IL-5 receptors following stimulation with IL-3 or IL-5, respectively (Woodcock et al, *Blood* 90:3005, 1997). Thirdly, specific mutations in the membrane proximal region of βc induce ligand-independent signaling yet depend on co-expression of the alpha subunit (D'Andrea et al, Blood 87:2641, 1996; Jenkins et al, *J. Biol. Chem.* 271:29707, 1996). Finally, the existence of βc, either on the cell membrane or in solution, as a non covalently-linked dimer is puzzling, particularly as the crystal structure of isolated βc revealed a dimer in which the cytoplasmic tails were 120 Å apart (Can et al, *cell* 104: 291, 2001). It is difficult to envisage how such a distance would allow transphosphorylation of βc by their associated JAK-2 kinases and downstream signaling.

There is a need to determine the structure of the GM-CSF and GM-CSFR complex and its role in signaling in order to rationally design therapeutic agents useful inter alia in treating inflammation, cardiovascular disease, ischemia, brain and heart infarcts, aberrant immunity, cancer including leukemia and infection by pathogenic agents.

SUMMARY

The present invention is predicated in part on the determination of the crystal structure of the GM-CSF/GM-CSFR ternary complex including its higher order forms revealing a 2:2:2 multimer consisting of two βc chains, two GM-CSFRα chains and two GM-CSF molecules or higher order forms thereof. Hence, in one embodiment, the higher order form is a dodecamer. The dimer in the complex is generated by crystallographic twofold axis which runs through the center of a hexameric complex. Each βc chain consists of two cytokine receptor homology molecules (CRMs), each of which consists of two fibronectin type III (FnIII) domains. Compared to the isolated βc chain, the complex has a domain 4 which is rotated 3° towards the crystallographic diad. The hinge region about which the rotation has occurred is located close to domain 1 in the linker region connecting domains 3 and 4. The GM-CSFRα chain consists of an N-terminal "knob" domain followed by one CRM.

The crystal structure reveals four main sites of interaction between surfaces and regions of GM-CSF and GM-CSFR designated Sites 1, 2, 3 and 4. Sites 2, 3 and 4 are located on the βc chain and Site 1 is on GM-CSFRα. It is proposed that agonists and antagonists of Sites 2, 3 and 4 will affect GM-CSF-mediated signaling as well as signaling of other cytokines such as IL-3, IL-5, EPO, TPO and c-kit ligand or derivatives thereof. An agonist or antagonist of Sites 1 to 4 will generally affect GM-CSF signaling. It is further proposed that Site 4 is required for the generation of higher order forms such as the dodecameric form. The agonists and antagonists need not directly interfere with Sites 1 to 4 but may interact elsewhere resulting in conformational changes to the sites.

In addition, the signaling characteristics between different higher order forms of the GM-CSF/GM-CSFR complex may have distinguishable properties. Hence, agonists and antagonists may be selected for specific forms of the receptor complex. In particular, an antagonist directed to Site 4 is proposed to inhibit higher order form generation and hence consequential signaling.

Accordingly, one aspect of the present invention provides a human GM-CSF/GM-CSFR crystalline complex having the atomic coordinates as set forth in Table 1. Generally, the crystalline complex comprising GM-CSF and GM-CSFR or their derivatives or components thereof are in essentially pure, native form. Derivatives and homologs, higher order forms and soluble forms of the crystalline complex or its components are also contemplated by the present invention. As indicated above, the various higher order forms may have different signaling properties. As indicated above, an example of a higher order form is a dodecamer.

Another aspect of the present invention is directed to a data set of atomic coordinates defining the ternary structure required for interaction between GM-CSF and GM-CSFR.

Yet another aspect of the present invention is directed to conformational mimetics of one or more of Sites 2, 3 and 4 on βc and Site 1 on GM-CSFRα useful as antagonists or agonists of GM-CSF signaling as well as signaling by one or more of IL-3, IL-5, erythropoietin (EPO), thrombopoietin (TPO) and/or c-kit ligand or their derivatives. As indicated above, the mimetics may interact or interfere directly at these sites or may interact elsewhere causing conformational changes to the sites or may influence the form or level of the complex. Antagonists of Sites 2, 3 and 4 on βc and Site 1 on GM-CSFRα are particularly contemplated herein. Even more particularly, the antagonist targets Site 4 and this disrupts dodecamer formation or the generation of other higher order forms.

Still even further more particularly, a Site 4 antagonist is proposed to reduce tyrosine phosphorylation of signaling mediators such as JAK-2, beta-c and STAT-5 in response to GM-CSF or other cytokine (e.g. Il; -3, IL-5, EPO, TPO) and consequently reduce cell proliferation.

Hence, in a particular embodiment, the present invention is directed to an agent which inhibits GM-CSF- or other cytokine-mediated signaling, the agent antagonizing a Site on a GM-CSF/CM-CSFR complex selected from Sites 1, 2, 3 and 4.

The targeting on Site 4 is particularly contemplated and such antagonists are proposed herein to be useful in treating inflammation (e.g. asthma) or cancer (e.g. leukemia). Examples of cancers and leukemias include those in which growth is induced by GM-CSF and/or IL-3.

Still another aspect of the present invention contemplates machine-readable media encoded with data representing the atomic coordinates of the three-dimensional structure of the GM-CSF/GM-CSFR crystalline form or a derivative or homolog thereof or its higher order or soluble form.

Another aspect of the present invention contemplates a process of identifying an agonist or an antagonist molecule comprising an entity selected from the group consisting of: a peptide, a non-peptide molecule and a chemical compound; wherein said molecule is capable of enhancing, eliciting or blocking the biological activity resulting from interaction with human GM-CSF and its receptor or derivatives thereof; wherein said process comprises: introducing into a suitable computer program parameters defining an interacting surface based on the conformation of human GM-CSF and/or GM-CSFRα corresponding to the coordinates of Table 1; wherein said program displays the three-dimensional structure thereof; creating a three-dimensional structure of a test compound in said computer program; displaying a superimposing model of said test compound on the model, assessing whether said test compound model fits spatially into the binding site; incorporating said test compound in a biological cytokine activity assay; and determining whether said test compound inhibits or enhances the biological activity of human GM-CSF or GM-CSFR signaling or signaling by a derivative thereof.

Antibodies and other agents which modulate GM-CSF/GM-CSFR interaction or signaling or which discriminate between lower or higher order forms of the GM-CSF/GM-CSFR complex also form part of the present invention as do antibodies to various derivative forms of GM-CSF or GM-CSFR.

A business model is also provided wherein potential agents are rationally designed based on one or more of:

1) access to the atomic coordinate set forth in Table 1;
2) knowledge and access to Site 1 on GM-CSFRα and/or Sites 2 through 4 on βc;
3) discriminatory antibodies to components of GM-CSF/GM-CSFR complex or higher order forms thereof or derivatives or homologs thereof or its soluble forms;
4) biological assays of GM-CSF antibody or signaling;

wherein said agents are evaluated as potential therapeutic agents which modulate the activity of GM-CSF, IL-3, IL-5, EPO, TPO and/or c-kit ligand signaling or signaling by derivatives thereof.

The present invention further contemplates an interactive data set of atomic coordinates as set forth in Table 1 (Example 1) when used to design agents which are capable of promoting or inhibiting or otherwise interacting with one or more of Sites 1 through 4 on GM-CSFRα or βc said interaction being interfaced by a computer program. Such agents may interact or interfere at one or more sites or may interact elsewhere causing conformational changes to the sites.

Another aspect of the present invention is directed to a computer program product for the rational design or selection of an agent which modulates GM-CSF or GM-CSFRα signaling, said product comprising:

(a) the atomic coordinates set forth in Table 1;
(b) optionally, knowledge of and access to Site 1 on GM-CSFRα and/or Sites 2 through 4 on βc;
(c) optionally, discriminatory antibodies to components of GM-CSF/GM-CSFR complex or higher order forms thereof or derivatives or homologs thereof or its soluble forms;
(d) optionally, biological assays of GM-CSF antibody or signaling;

(1) code that evaluates or ranks data; and
(2) a computer readable medium that stores the codes.

In a related embodiment, the present invention provides a computer for design or selection of agents wherein potentially modulate GM-CSF/GM-CSFR signaling, wherein said computer comprises:

(1) a machine-readable data storage medium comprising a data storage material encoded with machine-readable data, wherein said machine-readable data comprise features are selected from:—
   (a) the atomic coordinates set forth in Table 1;
   (b) optionally, knowledge of and access to Site 1 on GM-CSFRα and/or Sites 2 through 4 on βc;
   (c) optionally, discriminatory antibodies to components of GM-CSF/GM-CSFR complex or higher order forms thereof or derivatives or homologs thereof or its soluble forms;
   (d) optionally, biological assays of GM-CSF antibody or signaling;
(2) a working memory for storing instructions for processing said machine-readable data;
(3) a central-processing unit coupled to said working memory and to said machine-readable data storage medium, for processing said machine readable data to provide an evaluation data for said agent(s); and
(4) an output hardware coupled to said central processing unit.

The agents identified in accordance with the present invention are useful medicaments for the treatment of a range of conditions such as cancer, immune-based conditions, inflammatory conditions (e.g. asthma) and infection by pathogenic agents. Antibodies and other molecules which target and antagonize or agonize the function or activity or role of Site 1 or 2 or 3 or 4 are particularly contemplated herein.

Reference to GM-CSF and GM-CSFR and other cytokines or their receptors includes mutants and derivatives thereof.

Abbreviations used in the subject specification are defined in Table 2.

TABLE 2

Abbreviations

| Abbreviation | Definition |
|---|---|
| BC | Binary complex |
| βc | β Common receptor chain |
| CRM | Cytokine receptor module |
| D | Domain on a cytokine or receptor component |
| D"n"a-D"n"d | Domain number "n" on chain a, b, c or d of βc (referred to in the Figures) |
| EPO | Erythropoietin |
| FnIII | Fibronectin type III |
| GM-CSF | Granulocyte macrophage-colony stimulating factor |
| GM-CSFR/GMR | GM-CSF receptor |
| GM-CSFRα/GMRα | α-chain of GM-CSF receptor |
| GMR | GM-CSFR |
| GMRα | GM-CSFRα |
| IL-2 | Interleukin-2 |
| IL-3 | Interleukin-3 |
| IL-5 | Interleukin-5 |
| IL-6 | Interleukin-6 |
| SEQ ID NO: 1 | Amino acid sequence EARSWD present at Site 4 of βc |
| SEQ ID NO: 2 | Amino acid sequence AAAAAA present in mutant M7 of Site 4 of βc |
| TC | Ternary complex |
| TPO | Thrombopoietin |

Single and three letter abbreviations for amino acid residues used in the specification are defined in Table 3:

TABLE 3

Amino Acid Abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalamine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The position of an amino acid residue in a polypeptide or an amino acid substitution is given as "$Xaa^n$" wherein "Xaa" is an amino acid and "n" is the residue position or as "$Xaa_1nXaa_2$", wherein amino acid "$Xaa_1$" is replaced by "$Xaa_2$" at position "n".

BRIEF DESCRIPTION OF FIGURES

FIG. 1 is a diagrammatic representation of the structure of the GM-CSF receptor ternary complex. GM-CSF is highlighted in a dark shade and GM-C SFRα in a lighter shade. One monomer of βc is shown in one shade (chain a) and the other in another shade (chain b). Labels correspond to domain names. Orthogonal views show how the complex would sit on the membrane surface. The bottom panel shows the view of the receptor when looking towards the membrane and the top panel shows a side-on view with the molecule sitting on a membrane surface. Observed N-linked carbohydrates are shown as sticks. Disordered peptides that connect the C-termini of each chain to the membrane are shown as dashed lines in their respective shades. This and the following figures were prepared with PyMOL (DeLano, The PyMOL Molecular Graphics System, DeLano Scientific, San Carlos, Calif. USA, 2002).

FIG. 2 is a diagrammatic representation of the peeled-away interaction surfaces between components of the GM-CSF receptor. The surfaces are shaded colored by residue property: one shade is basic and another shade is acidic. Amino acids involved in the interfaces are labeled. The top panel shows how (βc interacts with GM-CSF (Site 2), the right middle panel shows the interaction between cytokine and GM-CSFRα (Site 1) and the bottom panel shows the interaction surfaces between (βc and GM-CSFRα (Site 3). A detailed view of GM-CSF Glu21 and 25 interacting residues of I3c is shown adjacent to the Site 2 panel.

FIGS. 3A and B are graphical representations showing that mutations of $Tyr^{421}$ in the FG loop of βc domain 4 abolish high-affinity binding of GM-CSF and IL-3 while mutations of the BC and FG loop of βc domain 4 reduce or abolish the proliferative response of CTL-EN cells to GM-CSF and IL-3 in clonal lines. (A) A graphical representation of Scatchard plots of $^{125}I$-labelled cytokine binding to COS cells expressing GM-CSFRα or IL-3Rα with wild type βc (●) or the Y421F (∇), Y421A (▲) βc mutants. The dashed line indicates the high affinity binding component for wild type βc and the solid line represents the line of best fit for the Y421F mutant βc as determined using the LIGAND program. (B) A graphical representation of cytokine mediated proliferation of CTL-EN cells stably expressing GM-CSFRα and IL-3Rα with either wild type βc (●) or the BC Poly-A (■), Y421A (▲), BC Poly-A+ Y421A (□) βc mutants. Proliferation is normalized against the maximum mIL-2 proliferation of each cell line. Data are the mean of triplicate determinations±standard deviation.

FIG. 4 is a diagrammatic representation showing the dodecamer complex. (A) View of the dodecamer when looking towards the membrane surface. Shading as in FIG. 1 with second hexamer in lighter shade. (A model of the complete domain 1 of GMRα (labeled αD1) was superimposed onto the partial model derived from the crystallographic data). Also shown is the likely location of the GM-CSFRα knob domain. In the lower panel a simplified representation highlights the arrangement of chains and domains adjacent to the membrane. The chains of βc are labeled a to d and domains denoted with a "D". (B) Side-on (with respect to the membrane) view of the complex, highlighting peeled-away interaction surfaces between GM-C SFRα domain 2 and βc domain 4's of each hexamer. (C) Model of signal transduction. The left hand panel shows the low affinity complex consisting of GM-C SF bound to GM-C SFRα. The high affinity complex forms through recruitment of βc (middle panel). Dodecamer (or higher order) complexes form by lateral aggregation of hexamer complexes to form a fully competent signaling complex (right panel).

FIG. 5 is a representation showing superposition of apo (light grey) (Carr et al, *Acta Crystallogr. F* 62:509, 2006) and complex (magenta) structures of βc highlighting a 3° rotation of domain 4 on complex formation.

FIG. 6 is a representation showing purified sβc ΔN3 titrated (1.2-10.7 μM) alone (B) or mixed with equimolar sGM-CSFRα and a 1.5× molar excess of GM-CSF (A). Chromatograms show reaction mixes set up with 2.1 μM, 4.3 μM, 6.5 μM, 8.6 μM or 10.7 μM sβc ΔN3, incubated at 25° C. for at least 1 hour and fractionated by size exclusion chromatography. Inset graphs plot the area of the peaks in min·mAU for ternary complex (TC), binary complex (BC) and free sβc (sβc) versus the elution time of each peak in minutes. Elution position of molecular weight standards is shown above each panel.

FIG. 7 is a representation showing comparison of related class I heteromeric cytokine receptor systems. Related receptor components in each of the three systems are highlighted by the same color where possible. (A) The GM-CSF receptor complex. The panel shows a blown-up view of part of the ternary complex in the same orientation presented in the top panel of FIG. 1. Also shown is the likely location of the GM-CSFRα knob domain. (B) The IL-6 receptor complex (Boulanger et al, supra 2003). For clarity only the unique components of the hexameric complex are shown with the exception of the second gp130 molecule where the N-terminal domain interacts with the cytokine molecule. (C) The IL-2 receptor complex (Wang et al, supra 2005).

FIG. 8 is a diagrammatic representation of IL-5 docking onto the GM-CSF receptor dodecamer complex. Structural superposition of the IL-5 dimer onto one of the GM-CSF molecules in the complex. Shown are (A) side and (B) top views.

FIG. 9 is a graphical representation of Scatchard plots of $^{125}$I-labeled GM-CSF binding to COS cells expressing GMRα with wild type βc ($^{430}$EARSWD$^{435}$ [SEQ ID NO:1]) or the βc4Gpoly-A mutant (M7-βc), ($^{430}$AAAAAA$^{435}$ [SEQ ID NO:2]). The lines indicate the high- and low-affinity binding components as determined using the KELL program and the affinity constants for the high-affinity sites are shown.

FIGS. 12A and B are graphical representations showing that the M7-βc mutation reduces the proliferative response of CTL-EN to GM-CSF and IL-3. The mIL2 dependant murine T-cell line, CTL-EN, expressing GMRα and IL3Rα was transfected to stably express wild type βc or M7-βc. Following starvation from mIL2 overnight, the proliferation of cell lines in response to GM-CSF (A) or IL-3 (B) was determined. Each point is determined in duplicate. Proliferation is normalized against the maximum mIL-2 proliferation of each cell line. Representative data are shown from multiple experiments: WT βc n=7, M7 βc n=8

FIGS. 13A and B are graphical representations showing that the M7-βc mutation reduces the proliferative response of CTL-EN cells to GM-CSF and IL-3 in clonal lines. Clones of CTL-EN cells (Clone 1, 2, 3, 4, 5, 6 and 8) were derived from a pool of CTL-EN cells expressing IL-3Rα, GMRα and M7-βc. Following starvation from mIL2 overnight, the proliferation of cell lines and clonal lines in response to GM-CSF (A) or IL-3 (B) was determined. Proliferation is normalized against the maximum mIL-2 proliferation of each cell line. Each point is determined in duplicate.

Figure 14:
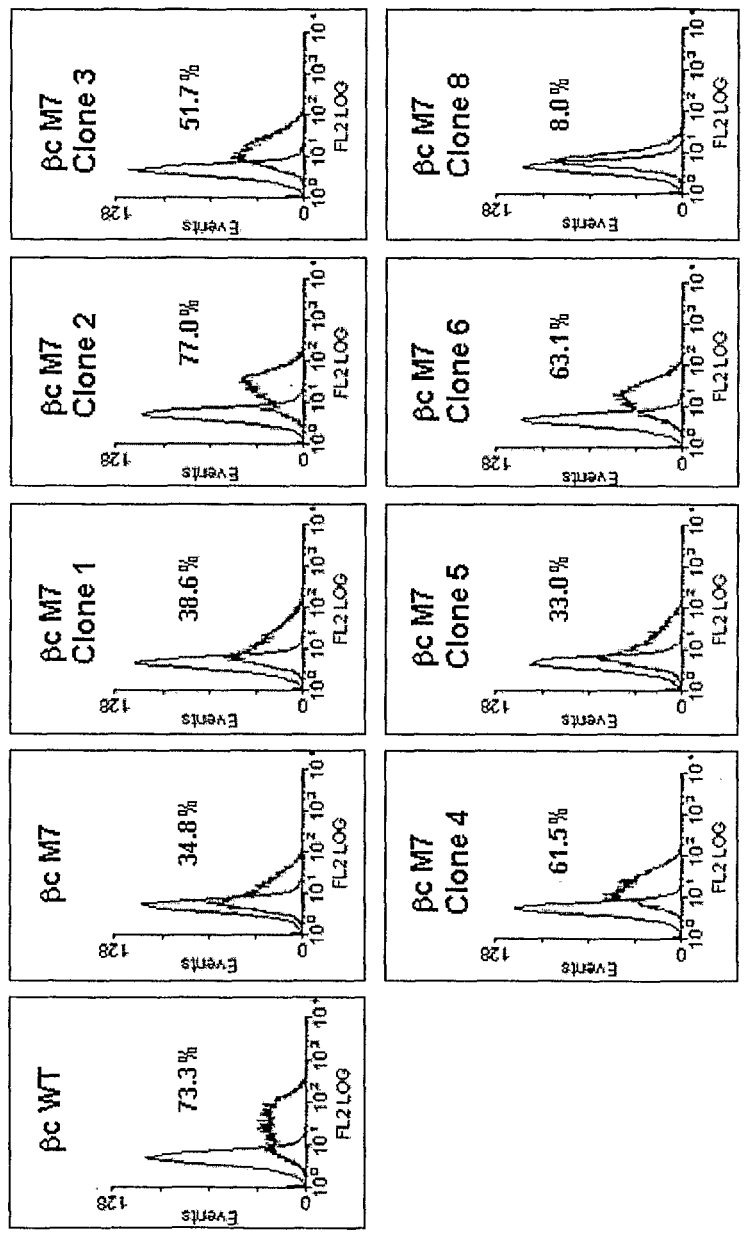

FIG. 14 is a graphical representation of flow cytometric analysis of CTL-EN cells expressing wild type βc or M7-βc as pools of cells or as clonal lines. Receptor expression was assessed using anti-βc specific monoclonal antibody, 1C1, (WTβc, M7βc) or isotype control (black). Representative data is shown from two independent analyses.

Figure 15:
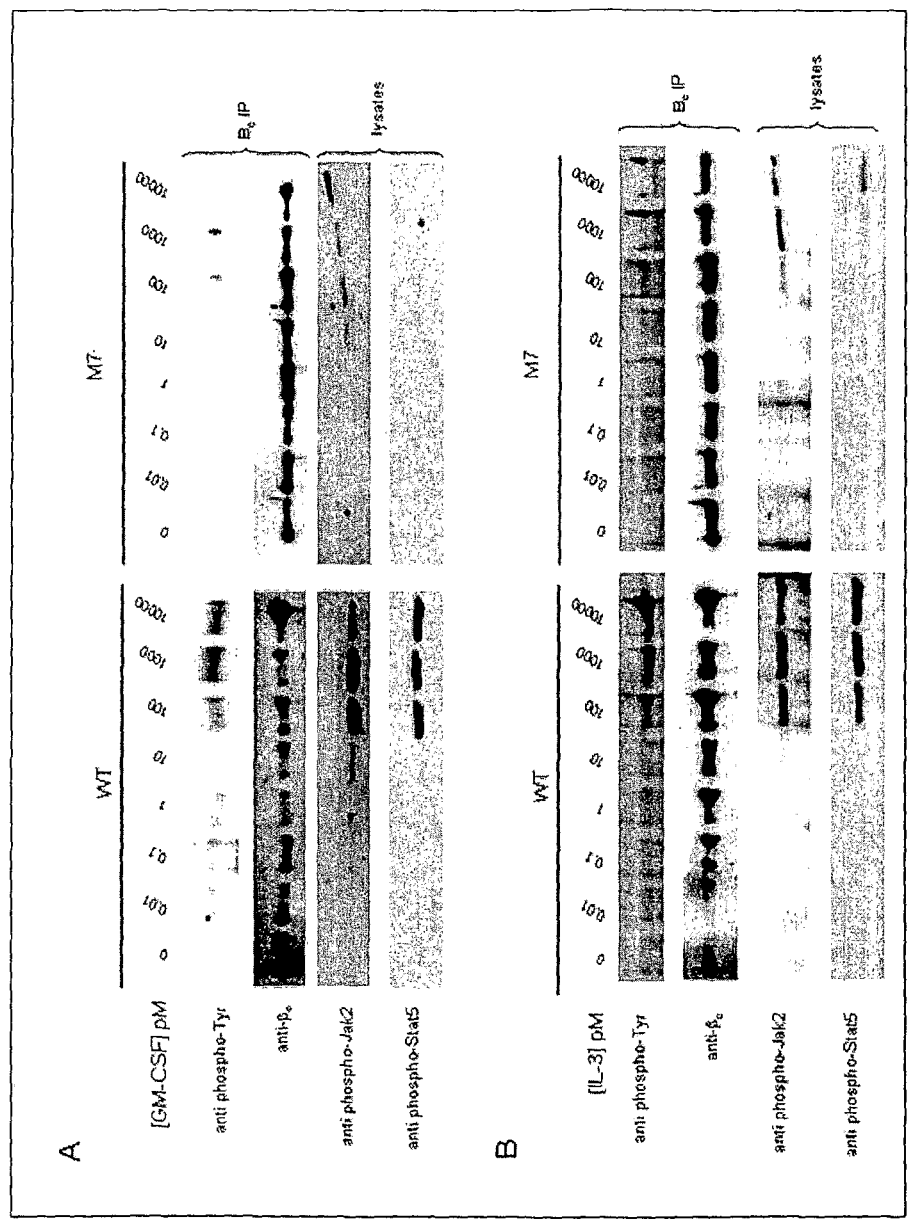

FIGS. 15A and B are photographic representations showing that a βc receptor mutated at Site 4 has a deficient capacity to be tyrosine phosphorylated in response to GM-CSF (A) or IL-3 (B). The tyrosine phosphorylation of two key signalling proteins, JAK-2 and STAT-5 was also determined.

DETAILED DESCRIPTION

In describing the present invention in detail, it is to be understood that unless otherwise indicated, the subject invention is not limited to specific cytokine or receptor components, manufacturing methods, crystallographic methods dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to "a complex" includes a single complex, as well as two or more complexes; reference to "an agent" includes a single agent, as well as two or more agents; reference to "the invention" includes a single and multiple aspects of the invention; and so forth.

Figure 1:
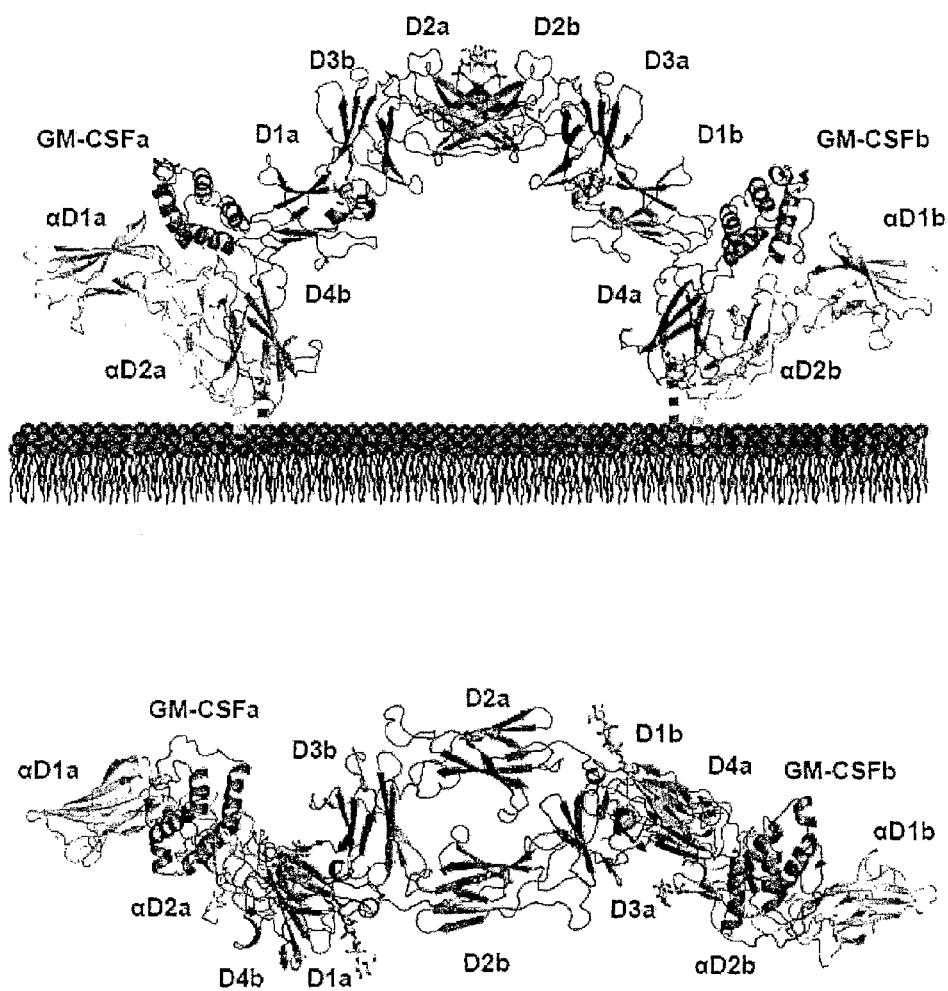

The present invention provides the crystal structure of a GM-CSF/GM-CSFR complex in the native form and substantially pure and refined to a resolution of 3.3 Å. The crystal structure reveals a ternary structure comprising a 2:2:2 hexamer consisting of two βc chains, two GM-CSFRα chains and two GM-CSF molecules. The structure is shown in FIG. 1. The βc homodimer is generated by a crystallographic twofold axis which runs through the center of the hexameric complex. Each βc chain consists of two cytokine receptor homology molecules (CRMs), each of which consists of two fibronectin type III (FnIII) domains. Compared to domain 4 in the isolated βc chain, the domain 4 of the βc chain in the complex is rotated towards the crystallographic diad. The hinge region about which the rotation has occurred is located close to domain 1 in the linker region connecting domains 3 and 4. The GM-CSFRα chain consists of an N-terminal "knob" domain followed by one CRM. However, well-defined electron density is only observed for the C-terminal FnIII domain of GM-CSFRα (GM-CSFRα domain 2). The complex comprises higher order forms such as a dodecameric form. It is proposed herein that some functional aspects of the complex such as signaling is facilitated by or requires higher order forms such as the dodecameric form.

There are four interactive sites, Site 1 to 4 in the receptor/ligand complex. These sites are described in detail below.

GM-CSF binds to the elbow region defined by domains 1 and 2 of GM-CSFRα, reminiscent of the binding mode seen in other class I cytokine receptors. There is a small interaction surface between GM-CSF and GM-CSFRα domain 2 of ~240 Å$^2$ per molecule with a surface complementarity of 0.66, a value within the range of normal protein-protein interaction surfaces. This is Site 1. Additional surface area would be provided by domain 1. The loop residues 241 to 251 and 299 to 305 of GM-CSFRα interact with residues 11 to 23 (Helix A) and residues 112 to 118 (Helix D) of GM-CSF.

Recruitment of βc to the GM-CSF:GM-CSFRα binary complex converts the GM-CSF binding to high affinity and leads to receptor activation. There is a second GM-CSF binding site (Site 2) at the elbow region between domain 1 (A-B and E-F loops) of one βc chain and domain 4 (B-C and F-G loops) of the second βc chain. The interaction at Site 2 buries ~570 Å$^2$ of surface area per molecule with a surface complementarity value of 0.62. Helix A of GM-CSF nestles into a surface crevice of βc formed by the E-F loop (residues 100 to 107) of βc domain 1 and the B-C (residues 360 to 369) and F-G (residues 417 to 423) loops of domain 4.

The principal cytokine interaction with βc occurs through a conserved glutamate in helix A of GM-CSF (Glu$^{21}$), IL-3 (Glu$^{22}$) or IL-5 (Glu$^{13}$). Glu$^{21}$ of GM-CSF is essential for high-affinity binding and function of GM-CSF as well as the direct physical association of GM-CSF with βc. No other βc contact residues in helix A of GM-CSF appear to be essential for function.

Domain 2 of GM-CSFRα forms an extensive interaction with domain 4 of βc resulting in ~680 Å$^2$ of buried surface area per molecule. The interface, involving residues 231, 232, 259, 266-270 and 280-286 of GM-CSFRα and residues 350, 353, 366-369, 389-400 and 418 of βc, is predominantly hydrophobic with a rim of charged residues (Site 3). The structure provided in accordance with the present invention shows that residues in the two hydrophobic surface patches in the crystal structure of the βc domain 4 (denoted H1 and H2; Rossjohn et al, *Blood* 95:2491, 2000). H2 is involved in the interface with GM-CSFRα. and H1 has contacts with βc. In particular, residues of H1 contact the A-B loop of domain 1 whereas residues of H2, located at the edge of the beta strands D and E of βc domain 4, are involved in the interface with GM-CSFRα. The Site 3 interface provides additional interacting surfaces between GM-CSFRα and βc thereby enhancing the overall binding affinity of GM-CSF for its receptor.

The crystal lattice generates an unexpected dodecamer complex consisting of two hexameric complexes related by a crystallographic twofold axis. Surprisingly, the dodecamer assembles in a head-to-head orientation bringing the C-terminal tails of neighboring βc domain 4's and GM-CSFRα domain 2's into close proximity suggesting a physiological relevance to the assembly. The interaction surface is large with ~770 Å$^2$ being buried per hexamer with major contributions between βc domain 4 of each hexamer (~520 Å$^2$ per molecule) and the rest contributed from an interaction between the GM-CSFRα of one hexamer and βc domain 4 of the other. The mostly polar interface involves residues 260 and 261 of GM-CSFRα and residues 346-354, 357, 359, 362, and 430-435 of βc with a high surface complementarity value of 0.63. This is Site 4. The βc domain 4 dodecamer interface includes the mutated N-linked glycosylation site, N346Q. Modeling two N-acetylglucosamine residues at this site shows that glycosylation is readily accommodated, increasing the contact area at the interface and potentially modulating signaling.

The active form of the GM-CSF/GM-CSFR complex is a higher order complex. Examples include but are not limited to a hexamer and a dodecamer. The various higher order forms of the cytokine/receptor complex may have different signaling properties.

A feature of the dodecamer structure is that the βc tails of adjacent hexamers are ~10 Å apart thus providing a molecular explanation of how GM-CSF binding can initiate receptor transphosphorylation through pairs of βc tails. Furthermore, in the dodecamer complex the GM-CSFRα cytoplasmic tails are ~30 Å from the βc cytoplasmic tails of each neighboring hexamer. Thus, the dodecamer structure also explains how the cytoplasmic domains from both subunits could participate in signaling.

Following structural rearrangement or misfolding, residues 395-431 of βc are available to functionally interact with GM-CSFRα in a cytokine-independent manner. Residues 395 to 400 of βc are located in the hexamer contact region with GM-CSFRα and supply the major surface for the Site 3 interaction between βc and GM-CSFRα. Dodecamer formation offers a unifying mechanism for ligand-dependent and -independent activation of the GM-CSF receptor.

Hence, the crystalline structure of the GM-CSF/GM-CSFR complex reveals four sites of interaction (Site 1 on GM-CSFRα and Sites 2, 3 and 4 on βc) which provide useful targets for modulators of GM-CSF signaling as well as signaling by IL-3, IL-5, EPO, TPO and c-kit ligand or derivatives thereof. The modulators may target directly any one or more of Sites 1 to 4 or may affect these sites indirectly via conformational changes following interaction at another site or region of the complex. The modulators may also discriminate between higher order forms of the cytokine/receptor complex.

Table 1 (in Example 1) provides the atomic coordinates of the native GM-CSF/GM-CSFR receptor complex. These coordinates were obtained using a model encompassing residues in the crystallographic dodecameric complex.

The atomic coordinates shown in Table 1 may change upon further refinement of the crystal structure, but the deviation that would occur as a result with regard to the Cα atoms is not expected to substantially exceed a root mean square (r.m.s.) of 1.0-1.5 Å. Similarly, bond angles and bond length will vary insignificantly as routinely observed with other proteins. With respect to the data collection for the GM-CSF/GM-CSFR crystalline complex, the space group is P6$_3$22 and cell dimensions are as follows:

a,b,c(Å):166.6, 166.6 and 213.1, respectively;
α, β, γ (degrees °): 90, 90 and 120, respectively.

With respect to refinement, the resolution is to 3.3 Å with 25,439 reflections and a $R$work/$R$free of 27.0/31.7%. The complex involves 5127 atoms and B-factors after TLS refinement for all atoms of 122.7 Å$^2$.

The term "r.m.s", as used herein, defines "root mean square".

Hence, the present invention provides a composition comprising GM-CSF/GM-CSFR complex in crystalline form or a derivative or homolog, higher order complex or soluble form thereof.

Particularly, the GM-CSF and GM-CSFR are each in an essentially pure native form or is a homolog or derivative thereof. The crystalline form is also substantially pure.

In a particular embodiment, the GM-CSF/GM-CSFR complex comprises a binding site (Site 1) on GM-CSFRα at an elbow region between domains 1 and 2 defined by loop residues 241 to 251 and 299 to 305 of GM-CSFRα which interact with residues 11 to 23 (Helix A) and residues 112 to 118 (Helix D) of GM-CSF.

Particularly, the GM-CSF/GM-CSFR complex comprises a binding site on GM-CSFR (Site 2) at the elbow region between domain 1 (A-B and E-F loops) of one βc and domain 4 (B-C and F-G loops) on a second βc wherein GM-CSF interacts with a surface crevice of βc formed by the E-F loops (residues 100 to 107) of βc domain 1 and the B-C (residues 360 to 369) and F-G (residues 417 to 423) loops of domain 4.

Particularly, the GM-CSFRα forms an interaction site (Site 3) for domain 4 of βc comprising residues 231, 232, 259, 266-270 and 280-286 of GM-CSFRα and residues 350, 353, 366-369, 389-400 and 418 of βc.

Particularly, the GM-CSF/GM-CSFR complex in situ forms a dodecamer or other high order complex via an interaction site (Site 4) between residues 260 and 261 of GM-CSFRα and residues 346-354, 357, 359, 362, and 430-435 of βc.

Particularly, the βc interactions through the Site 4 contact identified in the dodecamer complex appear to be required for GM-CSF and IL-3 signaling but not for high-affinity ligand binding.

The present invention is also directed to the use of the atomic coordinates of the three-dimensional structure of the GM-CSF/GM-CSFR crystalline form or its derivative or homolog or its higher order or soluble form in the design of agents which modulate GM-CSF/GM-CSFR interaction or signaling as well as signaling by one or more of IL-3, IL-5, EPO, TPO and/or c-kit ligand or derivatives thereof.

Furthermore, the present invention provides an interactive data set of atomic coordinates as set forth in Table 1 (Example 1) when used to design agents which are capable of promoting or inhibiting or otherwise interacting with one or more of Sites 1 through 4 on GM-CSFRα or βc said interaction being interfaced by a computer program. As indicated above, the agents may be designed or selected to interact or interfere with one or more of Sites 1 to 4 or may interact elsewhere causing conformational changes to any of the sites or influence the order of higher complex forms.

The present invention further contemplates a process of identifying an agonist or an antagonist molecule comprising an entity selected from the group consisting of: a peptide, a non-peptide molecule and a chemical compound; wherein said molecule is capable of enhancing, eliciting or blocking the biological activity resulting from interaction with human GM-CSF and its receptor; wherein said process comprises: introducing into a suitable computer program parameters defining an interacting surface based on the conformation of human GM-CSF and/or GM-CSFR corresponding to the coordinates of Table 1; wherein said program displays the three-dimensional structure thereof; creating a three-dimensional structure of a test compound in said computer program; displaying a superimposing model of said test compound on the model, assessing whether said test compound model fits spatially into the binding site; incorporating said test compound in a biological cytokine activity assay; and determining whether said test compound inhibits or enhances the biological activity of human GM-CSF or GM-CSFR signaling or signaling derivatives thereof.

Hence, the present invention further contemplates an interactive data set of atomic coordinates as set forth in Table 1 when used to design agents which are capable of promoting or inhibiting or otherwise interacting with one or more of Sites 1 through 4 on GM-CSFRα or βc said interaction being interfaced by a computer program.

The designing of mimetics to a pharmaceutically active compound is a known approach to the development of pharmaceuticals based on a "lead" compound. This might be desirable where the active compound is difficult or expensive to synthesize or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g. by substituting each residue in turn. Alanine scans of peptides are commonly used to refine such peptide motifs. These parts or residues constituting the active region of the compound are known as its "pharmacophore".

Once the pharmacophore has been found, its structure is modeled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modeling process.

In one approach, the atomic coordinates of three-dimensional structure are used for rational drug design. This can be especially useful where GM-CSF and/or GM-CSFR change conformation on binding or form higher order complexes allowing the model to take account of this in the design of the mimetic. Modeling can be used to generate modulators (activators and inhibitors) which interact with the linear sequence or a three-dimensional configuration.

A template molecule is generally selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

The goal of rational drug design is to produce structural analogs of biologically active polypeptides of interest or of small molecules with which they interact (e.g. agonists, antagonists, inhibitors or enhancers) in order to fashion drugs which are, for example, more active or stable forms of the polypeptide, or which, e.g. enhance or interfere with the function of a polypeptide in vivo. See, e.g. Hodgson, *BioTechnology* 9: 19-21, 1991. In one approach, one first determines the three-dimensional structure of a protein of interest by X-ray crystallography, by computer modeling or most typically, by a combination of approaches. Useful information regarding the structure of a polypeptide may also be gained by modeling based on the structure of homologous proteins. An example of rational drug design is the development of HIV protease inhibitors (Erickson et al, *Science* 249: 527-533, 1990). In addition, target molecules may be analyzed by an alanine scan (Wells, *Methods Enzymol.* 202: 2699-2705, 1991). In this technique, an amino acid residue is replaced by Ala and its effect on the peptide's activity is determined. Each of the amino acid residues of the peptide is analyzed in this manner to determine the important regions of the peptide.

The present invention contemplates, therefore, methods of screening for agents which modulate GM-CSF signaling. These molecules are also referred to herein as "targets", "a target" or "target molecule". The screening procedure includes assaying for the presence of a complex between the drug and the target. One form of assay involves competitive binding assays. In such competitive binding assays, the target is typically labeled. Free target is separated from any putative complex and the amount of free (i.e. uncomplexed) label is a measure of the binding of the agent being tested to target molecule. One may also measure the amount of bound, rather than free, target. It is also possible to label the compound rather than the target and to measure the amount of compound binding to target in the presence and in the absence of the drug being tested.

Another technique for drug screening provides high throughput screening for compounds having suitable binding affinity to a target and is described in detail in Geysen (International Patent Publication No. WO 84/03564). Briefly stated, large numbers of different small peptide test compounds are synthesized on a solid substrate, such as plastic pins or some other surface. The peptide test compounds are reacted with a target and washed. Bound target molecule is then detected by methods well known in the art. This method may be adapted for screening for non-peptide, chemical entities. This aspect, therefore, extends to combinatorial approaches to screening for target antagonists or agonists.

Purified target can be coated directly onto plates for use in the aforementioned drug screening techniques. However, non-neutralizing antibodies to the target may also be used to immobilize the target on the solid phase.

The present invention also contemplates the use of competitive drug screening assays in which antibodies capable of specifically binding the target compete with a test compound for binding to the target or fragments thereof. In this manner, the antibodies can be used to detect the presence of any peptide which shares one or more antigenic determinants of the target. The antibodies may also be used to discriminate between various higher order forms of the cytokine/receptor complex.

Hence, the present invention comprises a method for identifying agonists or antagonists of a human GM-CSF/GM-CSFR through the crystal structure herein described. The novel human GM-CSF/GM-CSFR crystalline structure of the invention permits the identification of agonists or antagonists of cytokine activity. Such antagonists may be competitive, binding to GM-CSF or GM-CSFR thereby preventing association of GM-CSF/GM-CSFR; or non-competitive and bind to and inhibit GM-CSF/GM-CSFR activity whether or not GM-CSF and GM-CSFR are associated.

One embodiment probes the human GM-CSF/GM-CSFR crystal of the invention with a variety of different chemical molecules to determine optimal sites either from interactions between such candidate agonist/antagonist molecules and human GM-CSF/GM-CSFR, or alternatively, for cellular activities. For example, high resolution X-ray diffraction data collected from crystals saturated with solvent allows the determination of binding positions for solvent molecule. Small molecules that would bind tightly to those sites can then be designed, synthesized and tested for their human GM-CSF/GM-CSFR agonist/antagonist activities.

Another embodiment screens computationally small molecule databases for chemical entities or compounds that can bind in whole, or in part, to human GM-CSF/GM-CSFR or both. This screening method and its utility is well known in the art. For example, such computer modelling techniques were described in a PCT application WO 97/16177.

Once identified by modelling, the agonist/antagonist may then be tested for biological activity. For example, the molecules identified may be introduced via standard screening formats into biological activity assays to determine the inhibitory activity of the compounds, or alternatively, binding assays to determine binding (Guthridge et al, supra 1998). One particularly preferred assay format is the enzyme-linked immunosorbent assay (ELISA). This and other assay formats are well known in the art and thus are not limitations to the present invention.

It is also possible to isolate a target-specific antibody including an antibody to a particular site or to different lower or higher order forms selected by a functional assay and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

The preferential binding of ligands to Sites 1 to 4, particularly with an affinity in the order of $10^{-8}$M or better, may arise from enhanced stereochemical complementarity relative to naturally-occurring ligands.

Pursuant to the present invention, such stereochemical complementarity is characteristic of a molecule which matches intra-site surface residues or other binding region identified herein. By "match" is meant that the identified portions interact with the surface residues, for example, via hydrogen bonding or by entropy-reducing van der Waals interactions which promote desolvation of the biologically active compound within the site, in such a way that retention of the biologically active compound within the groove is energetically favored.

It will be appreciated that it is not necessary that the complementarity between ligands and the site extend over all residues lining the surface in order to stabilise binding of the natural ligand. Accordingly, ligands which bind to some, but not all, of the residues lining the surface are encompassed by the present invention.

In general, the design of a molecule possessing stereochemical complementarity can be accomplished by means of techniques which optimize, either chemically or geometrically, the "fit" between a molecule and a target receptor. Suitable such techniques are known in the art. (See Sheridan and Venkataraghavan, *Acc. Chem. Res.* 20:322, 1987; Goodford, *J. Med. Chem.* 27:557, 1984; Beddell, *Chem. Soc. Reviews:*279, 1985; Hol, *Angew. Chem.* 25:767, 1986 and Verlinde, *W.G.J. Structure* 2:677, 1994, the respective contents of which are hereby incorporated by reference.)

Thus two approaches to designing a molecule according to the present invention include approaches which complement the shape of a target binding site. In the first of these, the geometric approach, the number of internal degrees of freedom, and the corresponding local minima in the molecular conformation space, is reduced by considering only the geometric (hard-sphere) interactions of two rigid bodies, where one body (the active site) contains "pockets" or "grooves" which form binding sites for the second body (the complementing molecule, as ligand). The second approach entails an assessment of the interaction of different chemical groups ("probes") with the active site at sample positions within and around the site, resulting in an array of energy values from which three-dimensional contour surfaces at selected energy levels can be generated.

The geometric approach is illustrated by Kuntz et al, *J. Mol. Biol.* 161:269-288, 1982, the contents of which are hereby incorporated by reference, whose algorithm for ligand design is implemented in a commercial software package distributed by the Regents of the University of California and further described in a document, provided by the distributor, entitled "Overview of the DOCK Package, Version 1.0,", the contents of which are hereby incorporated by reference. Pursuant to the Kuntz algorithm, the shape of the cavity represented by the copper-binding site is defined as a series of overlapping spheres of different radii. One or more extant databases of crystallographic data, such as the Cambridge Structural Database System maintained by Cambridge University (University Chemical Laboratory, Lensfield Road, Cambridge CB2 IEW, U.K) and the Protein Data Bank maintained by Brookhaven National Laboratory (Chemistry Dept. Upton, N.Y. 11973, U.S.A.), is then searched for molecules which approximate the shape thus defined.

Molecules identified in this way, on the basis of geometric parameters, can then be modified to satisfy criteria associated with chemical complementarity, such as hydrogen bonding, ionic interactions and van der Waals interactions.

The chemical-probe approach to ligand design is described, for example, by Goodford supra 1984, the contents of which are hereby incorporated by reference, and is implemented in several commercial software packages, such as GRID (product of Molecular Discovery Ltd., West Way House, Elms Parade, Oxford OX2 9LL, U.K.). Pursuant to this approach, the chemical prerequisites for a site-complementing molecule are identified at the outset, by probing the sites of interest with different chemical probes, e.g, water, a methyl group, an amine nitrogen, a carboxyl oxygen, and a hydroxyl.

Favored sites for interaction between the active site and each probe are thus determined, and from the resulting three-dimensional pattern of such sites a putative complementary molecule can be generated.

Programs suitable for searching three-dimensional databases to identify molecules bearing a desired pharmacophore include: MACCS-3D and ISIS/3D (Molecular Design Ltd., San Leandro, Calif.), ChemDBS-3D (Chemical Design Ltd., Oxford, U.K.), and Sybyl/3 DB Unity (Tripos Associates, St. Louis, Mo.).

Programs suitable for pharmacophore selection and design include: DISCO (Abbott Laboratories, Abbott Park, Ill.), Catalyst (Bio-CAD Corp., Mountain View, Calif.), and ChemDBS-3D (Chemical Design Ltd., Oxford, U.K.).

Databases of chemical structures are available from a number of sources including Cambridge Crystallographic Data Centre (Cambridge, U.K.) and Chemical Abstracts Service (Columbus, Ohio).

De novo design programs include Ludi (Biosym Technologies Inc., San Diego, Calif.), Sybyl (Tripos Associates) and Aladdin (Daylight Chemical Information Systems, Irvine, Calif.).

Those skilled in the art will recognize that the design of a mimetic compound may require slight structural alteration or adjustment of a chemical structure designed or identified using the methods of the invention.

This aspect of the present invention may be implemented in hardware or software, or a combination of both. However, the subject invention is preferably implemented in computer programs executing on programmable computers each comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object-oriented programming language to communicate with a computer system. However, the programs can be implemented in assembly or machine language, if desired. In any case, the language may be compiled or interpreted language.

Each such computer program is preferably stored on a storage medium or device (e.g, ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

In another aspect, the invention contemplates a computer program product for the rational design or selection of an agent which modulates GM-CSF or GM-CSFR signaling, said product comprising:
  (e) the atomic coordinates set forth in Table 1;
  (f) optionally, knowledge of and access to Site 1 on GM-CSFRα and/or Sites 2 through 4 on βc;
  (g) optionally, discriminatory antibodies to components of GM-CSF/GM-CSFR complex or higher order forms thereof or derivatives or homologs thereof or its soluble forms;

(h) optionally, biological assays of GM-CSF antibody or signaling;

(3) code that evaluates or ranks data; and (4) a computer readable medium that stores the codes.

In a related aspect, the invention extends to a computer for design or selection of agents wherein potentially modulate GM-CSF/GM-CSFR signaling, wherein said computer comprises:

(5) a machine-readable data storage medium comprising a data storage material encoded with machine-readable data, wherein said machine-readable data comprise features are selected from:—

(e) the atomic coordinates set forth in Table 1;
(f) optionally, knowledge of and access to Site 1 on GM-CSFRα and/or Sites 2 through 4 on βc;
(g) optionally, discriminatory antibodies to components of GM-CSF/GM-CSFR complex or higher order forms thereof or derivatives or homologs thereof or its soluble forms;
(h) optionally, biological assays of GM-CSF antibody or signaling;
(6) a working memory for storing instructions for processing said machine-readable data;
(7) a central-processing unit coupled to said working memory and to said machine-readable data storage medium, for processing said machine readable data to provide an evaluation data for said agent(s); and
(8) an output hardware coupled to said central processing unit.

In one version of these embodiments, a system including a computer comprising a central processing unit ("CPU"), a working memory which may be, e.g. RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bidirectional system bus.

Input hardware, coupled to computer by input lines, may be implemented in a variety of ways. For example, machine-readable data of this invention may be inputted via the use of a modem or modems connected by a telephone line or dedicated data line. Alternatively or additionally, the input hardware may comprise CD. Alternatively, ROM drives or disk drives in conjunction with display terminal, keyboard may also be used as an input device.

Output hardware, coupled to computer by output lines, may similarly be implemented by conventional devices. By way of example, output hardware may include CRT display terminal for displaying a synthetic polynucleotide sequence or a synthetic polypeptide sequence as described herein. Output hardware might also include a printer, so that hard copy output may be produced, or a disk drive, to store system output for later use.

In operation, CPU coordinates the use of the various input and output devices coordinates data accesses from mass storage and accesses to and from working memory, and determines the sequence of data processing steps. A number of programs may be used to process the machine readable data of this invention. Exemplary programs may use, for example, the following steps:—
(1) inputting data features associated with said agent(s), wherein said features are selected from:
(a) the atomic coordinates set forth in Table 1;
(b) optionally, knowledge of and access to Site 1 on GM-CSFRα and/or Sites 2 through 4 on βc;
(c) optionally, discriminatory antibodies to components of GM-CSF/GM-CSFR complex or higher order forms thereof or derivatives or homologs thereof or its soluble forms;
(d) optionally, biological assays of GM-CSF antibody or signaling;
(2) adding evaluation data for said features to provide a ranking or selection; and
(3) outputting data.

The present invention further provides a magnetic data storage medium which can be encoded with machine readable data, or set of instructions, for designing a synthetic molecule of the invention, which can be carried out by a system such as described above. Medium can be a conventional floppy diskette or hard disk, having a suitable substrate, which may be conventional, and a suitable coating, which may be conventional, on one or both sides, containing magnetic domains whose polarity or orientation can be altered magnetically. Medium may also have an opening for receiving the spindle of a disk drive or other data storage device. The magnetic domains of coating of medium are polarised or oriented so as to encode in manner which may be conventional, machine readable data such as that herein described.

The present invention also provides an optically readable data storage medium which also can be encoded with such a machine-readable data, or set of instructions, for designing a synthetic molecule of the invention, which can be carried out by a system. Medium can be a conventional compact disk read only memory (CD-ROM) or a rewritable medium such as a magneto-optical disk, which is optically readable and magneto-optically writable. Medium preferably has a suitable substrate, which may be conventional, and a suitable coating, which may be conventional, usually of one side of substrate.

In the case of CD-ROM, as is well known, coating is reflective and is impressed with a plurality of pits to encode the machine-readable data. The arrangement of pits is read by reflecting laser light off the surface of coating. A protective coating, which preferably is substantially transparent, is provided on top of coating.

In the case of a magneto-optical disk, as is well known, coating has no pits, but has a plurality of magnetic domains whose polarity or orientation can be changed magnetically when heated above a certain temperature, as by a laser. The orientation of the domains can be read by measuring the polarization of laser light reflected from coating. The arrangement of the domains encodes the data as described above.

The agents identified by the present invention are useful for generating or designing derivatives of GM-CSF or GM-CSFR, identifying homologs thereof and for determining the crystal structure of variant forms of GM-CSF and/or GM-CSFR. Such molecules are useful for modulating the signaling of cytokines such as GM-CSF, IL-3, IL-5, EPO, TPO and c-kit ligand or their derivatives.

The term "cytokine", as used herein, means a protein modulating the growth and functional activities of hematopoietic cells as well as dendritic cells and T-cells. Reference to a cytokine or its receptor or specifically GM-CSF, GM-CSFR, GM-CSFRα, βc, IL-3, IL-5, EPO, TPO and c-kit ligand includes derivatives and mutants and polymorphic or homolog forms thereof.

The term "homolog", as used herein, means a protein having at least 30% amino acid sequence identity with a functional domain of human GM-CSF or GM-CSFRα or βc. Preferably the percentage identity is 40 or 50%, more preferably 60 or 70% and most preferably 80 or 90%. A 95% or above identity is most particularly preferred such as 95%, 96%, 97%, 98%, 99% or 100%.

A "binary complex" or "BC" is used to define a GM-CSF and GM-CSFRα complex. A "ternary complex" or "TC" is a complex between GM-CSF, GM-CSFRα and βc.

A "higher order complex" is a term used to describe a multimer of the ternary complex and includes but is not limited to a hexamer complex of two GM-CSF, two GM-CSFRα and two βc molecules and a dodecamer complex which contains two hexamers. A higher order complex also includes a co-complex of one or more components of the GM-CSF/GM-CSFR complex and another molecule. Various higher order complexes may have different signaling properties.

Hence, the term "co-complex", as used herein, means the human GM-CSF and/or GM-CSFR or a derivative or homolog thereof in covalent or non-covalent association with a chemical entity or compound.

The term "derivative", as used herein, means the GM-CSF and/or GM-CSFR polypeptide complexes displaying the biological activity of wild-type GM-CSF/GM-CSFR interaction, characterized by the replacement of at least one amino acid from the wild-type sequence. Such a derivative may be prepared, for example, by expression of the human GM-CSF/GM-CSFR cDNA previously altered in its coding sequence by oligonucleotide-directed mutagenesis. The terms "derivative" and "mutant" may be used interchangeably. A derivative also includes a heavy atom derivative.

Other forms of the GM-CSF/GM-CSFR complex include soluble forms, such as molecules which have been cross-linked.

Crosslinkers can be used, for example, to stabilize 3D conformations, using homo-bifunctional crosslinkers such as the bifunctional imido esters having ($CH_2$), spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The term "molecular replacement", as used herein, means a method of solving crystal structure using the atomic coordinates of a structurally related molecule.

Human GM-CSF/GM-CSFR mutants may also be generated by site-specific incorporation of unnatural amino acids into the human GM-CSF and/or GM-CSFR protein using the general biosynthetic method such as Noren et al, *Science* 244:182-188, 1989. In this method, the nucleotides encoding the amino acid of interest in wild-type GM-CSF and/or GM-CSFR is replaced by a "blank" nonsense codon, TAG, using oligonucleotide-directed mutagenesis. A suppressor directed against this codon, is then chemically aminoacylated in vitro with the desired unnatural amino acid. The aminoacylated residue is then added to an in vitro translation system to yield a mutant human GM-CSF/GM-CSFR enzyme with the site-specific incorporated unnatural amino acid.

Examples of unnatural amino acids are listed in Table 4.

TABLE 4

Unnatural Amino Acids

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |

TABLE 4-continued

Unnatural Amino Acids

| Non-conventional amino acid | Code | Non-conventional amino acid | Code |
|---|---|---|---|
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

The present invention contemplates, therefore, chemical analogs of the polypeptide components of the GM-CSF/GM-CSFR complex capable of acting as antagonists or agonists of GM-CSF signaling. Chemical analogs may not necessarily be derived from the present polypeptides in the GM-CSF/GM-CSFR complex but may share certain conformational similarities. Alternatively, chemical analogs may be specifically designed to mimic certain physiochemical properties of the subject GM-CSF/GM-CSF components molecules. Chemical analogs may be chemically synthesized or may be detected following, for example, natural product screening. Generally, the antagonists and agonists are rationally designed using the coordinates in Table 1.

Other derivatives contemplated by the present invention include a range of glycosylation variants from a completely unglycosylated molecule to a modified glycosylated molecule. Altered glycosylation patterns may result from expression of recombinant molecules in different host cells.

The present invention extends to antibodies and other immunological agents directed to or which are specific for the GM-CSF/GM-CSFR complex or a component thereof or a particular level of complex or a fragment thereof. The antibodies may be monoclonal or polyclonal or may comprise Fab fragments or synthetic forms or single chain forms. Antibodies may be specific for GM-CSFRα or βc or a complex of both. Agents which bind to the same epitope or which compete with antibodies binding are also contemplated herein.

Antibodies include any immunological agent and hence may be referred to as immunointeractive molecules. An antibody specific for a site selected from Site 2, Site 3 and Site 4 of β and Site 1 of GM-CSFRα is particularly contemplated herein.

Hence, the present invention relates to isolated monoclonal or polyclonal antibodies, particularly human monoclonal antibodies, that bind to a site on βc selected from Site 2, Site 3 and Site 4 or on GM-CSFRα selected from Site 1 and which inhibit certain functional properties of GM-CSF/GM-CSFR signaling. Reference to the instant "monoclonal antibodies" includes humanized, deimmunized and chimeric forms thereof as well as mammalianized which includes primatized forms. In certain embodiments, the antibodies of the present invention comprise particular structural features such as CDR regions comprising particular amino acid sequences. The present invention provides isolated antibodies, methods of making such antibodies, immunoconjugates and bispecific molecules comprising such antibodies and pharmaceutical compositions containing the antibodies, immunconjugates or bispecific molecules of the invention. The subject invention also relates to methods of using the antibodies to inhibit cytokine signaling such as mediated via GM-CSF, IL-3, IL-5, EPO or TPO, for example in the treatment of disorders and diseases including inflammation, cardiovascular disease, ischemia, brain and heart infarcts, aberrant immunity, cancer including leukemia and infection by pathogenic agents.

In generating the antibodies of the present invention, antibodies to Site 4 and which inhibit higher order form generation (e.g. dodecamer formation) are particularly useful.

The term "antibody" as referred to herein includes whole antibodies (also known as full-length antibodies) and any antigen binding fragment (i.e., "antigen-binding portion") thereof. A "whole antibody" refers to a glycoprotein comprising two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, $C_{H1}$, $C_{H2}$ and $C_{H3}$. Each light chain is comprised of a light chain variable region (abbreviated herein as VL) and a light chain constant region. The light chain constant region is comprised of one domain, $C_L$. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order:FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g, effector cells) and the first component (C1q) of the classical complement system.

The term "antigen-binding portion" of an antibody, as used herein, refers to one or more fragments of an antibody that retain the ability to bind to GM-CSFR, βc or GM-CSF or a site thereon or on the complex thereof. The antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the VH and $C_{H1}$ domains; (iv) a Fv fragment consisting of the VL and VH domains of a single arm of an antibody, (v) a dAb fragment (Ward et al, *Nature* 341:544-546, 1989), which consists of either a VH or a VL domain (Holt et al, *Trends in Biotechnology,* 21:484-489, 2003); and (vi) an isolated complementarity determining region (CDR), in particular CDR3 of a VH. As will be appreciated by those skilled in the art fragments of an antibody that retain the ability to bind to one of Sites 1 through 4 may be inserted into various frameworks, see for example U.S. Pat. No. 6,818,418 and references contained therein which discuss various scaffolds which may be used to display antibody loops previously selected on the basis of antigen binding. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g, Bird et al, *Science* 242:423-426, 1988 and Huston et al, *Proc. Natl. Acad. Sci. USA* 85:5879-5883, 1988). Such single chain antibodies are also intended to be encompassed within the term "antigen-binding portion" of an antibody. These antibody fragments may be obtained using conventional techniques known to those with skill in the art, and may be produced without having first produced a full-length antibody. Fragments may be screened for relevant properties in the same manner as are full-length antibodies.

An "isolated antibody", as used herein, is intended to refer to an antibody that is substantially free of other antibodies having different antigenic specificities (e.g, an isolated antibody that binds to one of Sites 1 through 4 is substantially free of antibodies that bind antigens other than one of these sites). An isolated antibody that binds Site 4 may, however, have cross-reactivity to other sites, or sites on GM-CSF/GM-CSFR complexes from other species. Moreover, an isolated antibody may be substantially free of other cellular material and/or chemicals.

The term "monoclonal antibody" or "mAb" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. A monoclonal antibody that is also an isolated antibody may be referred to as an isolated monoclonal antibody. Deimmunized and chimeric antibodies are also contemplated as are mammalianized including primatized forms of the antibodies.

The term "human antibody", as used herein, is intended to include antibodies having variable regions derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g, mutations introduced by random or site-specific mutagenesis in vitro or by somatic mutation in vivo), for example in the CDRs and in particular CDR3 and thus the amino acid sequences of the VL and/or VH regions of the antibodies are sequences that, while derived from and related to human germline VL and VH sequences, may not naturally exist within the human antibody germline repertoire in vivo. However, the term "human antibody", as used herein, is not intended to include antibodies in which CDR sequences derived from another mammalian species, such as a mouse, have been grafted onto human framework sequences; i.e. a humanized antibody.

As used herein, "isotype" refers to the antibody class (e.g, IgM or IgG1) that is encoded by the heavy chain constant region genes.

Hence, another aspect of the present invention provides an antibody or derivative or deimmunized or humanized (or primatized) form thereof which binds to Site 1 on GM-CSFRα at an elbow region between domains 1 and 2 defined by loop residues 245 to 251 and 299 to 305 of GM-CSFRα which interact with residues 11 to 23 (Helix A) and residues 112 to 118 (Helix D) of GM-CSF or an agent which competes with the binding of the antibody.

Another aspect provides an antibody or derivative or chimeric or deimmunized or humanized (or primatized) form thereof which binds to Site 2 on βc at the elbow region between domain 1 (A-B and E-F loops) of one βc and domain 4 (B-C and F-G loops) on a second βc wherein GM-CSF interacts with a surface crevice of βc formed by the E-F loops (residues 100 to 107) of βc domain 1 and the B-C (residues 360 to 369) and F-G (residues 417 to 423) loops of domain 4 or an agent which competes with the binding of the antibody.

Still a further aspect provides an antibody or derivative or chimeric or deimmunized or humanized (or primatized) form thereof which binds to Site 3 at domain 4 of βc comprising residues 231, 232, 259, 266-270 and 280-286 of GM-CSFRα and residues 350, 353, 366-369, 389-400 and 418 of βc or an agent which competes with the binding of the antibody.

Yet another aspect is directed to an antibody or derivative or chimeric or deimmunized or humanized (or primatized) form thereof which binds to Site 4 between residues 260 and 261 of GM-CSFRα and residues 346-354, 357, 359, 362, and 430-435 of βc or an agent which competes with the binding of the antibody.

One particular group of antibodies of the subject invention are those that inhibit higher order complex form generation such as dodecamer formation or which otherwise reduce the capacity to phosphorylate tyrosine residues in response to GM-CSF or other cytokine such as IL-3, IL-5, EPO or TPO. Such antibodies particularly target Site 4 and are contemplated herein.

As indicated above, particular, antibodies of the present invention are human antibodies. In another embodiment, the antibodies are humanized, deimmunized, mammalianized including primatized or chimeric antibodies.

Antibodies of the subject invention may be of any antibody isotype, e.g. IgG, IgA, IgE and IgM and any of the isotype sub-classes, particularly IgG1 and IgG4. IgG4 is preferred because it does not bind complement and does not create effector functions. Any synthetic or other constant region variant that has these or other desirable properties is also preferred for use in embodiments of the present invention.

Standard assays to evaluate the binding ability of the antibodies toward a fragment or site on GM-CSF/GM-CSFR of various species are known in the art, including for example, ELISAs, Western blots and RIAs. Examples of suitable assays are described in the Examples. The binding kinetics (e.g, binding affinity) of the antibodies also can be assessed by standard assays known in the art, such as by Biacore (Trademark) analysis.

Accordingly, an antibody that "inhibits" signaling or other functional properties of GM-CSF/GM-CSFR complex formation as determined according to methodologies known to the art will be understood to relate to a decrease in the particular activity relative to that seen in the absence of the antibody (e.g., when a control antibody of irrelevant specificity is present). In one example, an antibody that inhibits a GM-CSF signaling effects such a decrease by at least 10% of the measured parameter, more preferably by at least 20%, 30%, 40%, 50%, 60%, 70%, 80%, 90% or 95%. This can be determined by, for example, growth of GM-CSF-dependent cell lines, phosphorylation assays and the like.

An antibody of the present invention can be prepared using an antibody having one or more of the VH and/or VL sequences as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region modification is to mutate amino acid residues within the VH and/or VL CDR1, CDR2 and/or CDR3 regions to thereby improve one or more properties (e.g. binding affinity) of the antibody of interest. Site-directed mutagenesis or random mutagenesis can be performed to introduce the mutation(s) and the effect on antibody binding, or other functional property of interest, can be evaluated in in vitro or in vivo assays. The mutations may be amino acid substitutions, additions or deletions, but are preferably substitutions. Moreover, typically no more than one, two, three, four or five residues within a CDR region are altered, preferably only one or two residues within the VH and/or VL CDR1, CDR2 and/or CDR3 regions are altered.

Antibodies of the instant invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent No. 20030153043.

In addition or alternative to modifications made within the framework or CDR regions, antibodies of the present invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g, one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat et al, *Sequences of Proteins of Immunological Interest, Fifth Edition, U.S. Department of Health and Human Services, NIH Publication No.* 91:3242, 1991.

In one embodiment, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the antibody is modified to increase its biological half life. Various approaches are possible such as described in U.S. Pat. No. 6,277,375. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet another embodiment, the Fc region is altered by replacing at least one amino acid residue with a different amino acid residue to alter the effector function(s) of the antibody. The effector ligand to which affinity is altered can be, for example, an Fc receptor or the C1 component of complement. This approach is described in further detail in U.S. Pat. Nos. 5,624,821 and 5,648,260.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1 176 195 describes a cell line with a functionally disrupted FUT8 gene, which encodes a fucosyl transferase, such that antibodies expressed in such a cell line exhibit hypofucosylation. PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al, *J. Biol. Chem.* 277:26733-26740, 2002). PCT Publication WO 99/54342 describes cell lines engineered to express glycoprotein-modifying glycosyl transferases (e.g, beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al, *Nat. Biotech.* 17:176-180, 1999).

Another modification of the antibodies herein that is contemplated by the invention is pegylation. An antibody can be pegylated to, for example, increase the biological (e.g, serum) half life of the antibody, or an antigen binding portion thereof. To pegylate an antibody, the antibody typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 and EP 0 401 384.

Monoclonal antibodies of the present invention can be produced by a variety of techniques, including conventional monoclonal antibody methodology e.g, the standard somatic cell hybridization technique of Kohler and Milstein, *Nature* 256:495, 1975. Although somatic cell hybridization procedures are preferred, in principle, other techniques for producing monoclonal antibody can be employed e.g, viral or oncogenic transformation of B lymphocytes.

One animal system for preparing hybridomas is the murine system. Hybridoma production in the mouse is a very well-established procedure. Immunization protocols and techniques for isolation of immunized splenocytes for fusion are known in the art. Fusion partners (e.g, murine myeloma cells) and fusion procedures are also known.

Chimeric, humanized or primatized antibodies of the present invention can be prepared based on the sequence of a murine monoclonal antibody prepared using standard molecular biology and generally in accordance with the description herein. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567). To create a humanized antibody, the murine CDR regions can be inserted into a human framework using methods known in the art (see e.g, U.S. Pat. No. 5,225,539 and U.S. Pat. Nos. 5,530,101; 5,585,089; 5,693,762 and 6,180,370). Similarly, to create a primatized antibody the murine CDR regions can be inserted into a primate framework using methods known in the art (see e.g. WO 93/02108 and WO 99/55369).

Alternatively, a humanized antibody may be created by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan et al, *Mol. Immunol.* 28:489-498, 1991 and Pedersen et al, *J. Mol. Biol.* 235:959-973, 1994). Therefore, it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region "invisible" to the human immune system (see also Mark et al, *Handbook of Experimental Pharmacology vol.* 113: The pharmacology of monoclonal Antibodies, Springer-Verlag, pp 105-134, 1994). This procedure of humanization is referred to as "veneering" because only the surface of the antibody is altered, the supporting residues remain undisturbed.

Further, WO 2004/006955 describes methods for humanizing antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO 2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

In an embodiment, the antibodies of the present invention are human monoclonal antibodies. Such human monoclonal antibodies directed against one of Sites 1 through 4 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse™ [Medarex, Inc.] contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al, *Nature* 368(6474):856-859, 1994). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg et al, 1994, supra; reviewed in Lonberg, *Handbook of Experimental Pharmacology* 113:49-101, 1994; Lonberg and Huszar, *Intern. Rev. Immunol.* 13:65-93, 1995, and Harding and Lonberg, *Ann. N.Y. Acad. Sci.* 764: 536-546, 1995). The preparation and use of HuMab mice, and the genomic modifications carried by such mice, is further described in Taylor et al, *Nucleic Acids Research* 20:6287-6295, 1992; Chen et al, *International Immunology* 5:647-656, 1993; Tuaillon et al, *Proc. Natl. Acad. Sci. USA* 90:3720-3724, 1993; Choi et al, *Nature Genetics* 4:117-123, 1993; Chen et al, *EMBO J.* 12:821-830, 1993; Tuaillon et al, *J. Immunol.* 152:2912-2920, 1994; Taylor et al, *International Immunology* 6:579-591, 1994; and Fishwild et al, *Nature Biotechnology* 14:845-851, 1996, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; 5,545,807; PCT Publication Nos. WO 92/03918, WO 93/12227, WO 94/25585, WO 97/13852, WO 98/24884 and WO 99/45962 and WO 01/14424.

In another embodiment, human antibodies of the subject invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; 5,571, 698; 5,427,908; 5,580,717; 5,969,108; 6,172,197; 5,885,793; 6,521,404; 6,544,731; 6,555,313; 6,582,915; and 6,593,081.

In another aspect, the present invention features bispecific molecules comprising antibodies specific for two or more of Sites 1 through 4. An antibody of the invention can be derivatized or linked to another functional molecule, e.g., another peptide or protein (e.g, another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g, by chemical coupling, genetic fusion, noncovalent association or otherwise) to one or more other binding molecules, such as another antibody, antibody fragment, peptide or binding mimetic, such that a bispecific molecule results.

The present invention further extend to agents which are antagonists of one or more of Sites 1 through 4 and which compete with the binding of the subject antibody.

Antibodies (and immunoconjugates and bispecific molecules) or small molecules or proteinaceous agonists or antagonists of the present invention (e.g. those which compete for binding with antibodies) may be used in methods of treatment or diagnosis in human or animal subjects. Antagonists are particularly useful for treating inflammation (e.g. asthma), cardiovascular disease, ischemia, infarcts of the brain or heart, aberrant immunity, cancer including leukemia and infection by pathogenic agents.

Accordingly, further aspects of the present invention provide methods of treatment comprising administration of antibodies (and immunoconjugates and bispecific molecules and antagonists) as provided, pharmaceutical compositions comprising such antibodies (and immunoconjugates and bispecific molecules and antagonists), and use of antibodies (and immunoconjugates and bispecific molecules) in the manufacture of a medicament for administration, for example in a method of making a medicament or pharmaceutical composition comprising formulating the antibodies (and immunoconjugates and bispecific molecules) with a pharmaceutically acceptable excipient for the treatment, inter alia of inflammation (e.g. asthma), cardiovascular disease, ischemia, infarcts of the brain or heart, aberrant immunity, cancer including leukemia and infection by pathogenic agents.

Specific antibodies can also be used to screen for the subject GM-CSF/GM-CSFR complex or its various forms of components thereof. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies referred to above. Both the first and second antibodies may be used in detection assays or a first antibody may be used with a commercially available anti-immunoglobulin antibody. An antibody as contemplated herein includes any antibody specific to any region of GM-CSF or GM-CSFR or a complex or component thereof.

Both polyclonal and monoclonal antibodies are obtainable by immunization with GM-CSF or GM-CSFR or components thereof or antigenic fragments thereof and either type is utilizable for immunoassays. The methods of obtaining both types of sera are well known in the art. Polyclonal sera are less preferred but are relatively easily prepared by injection of a suitable laboratory animal with an effective amount of subject polypeptide, or antigenic parts thereof, collecting serum from the animal and isolating specific sera by any of the known immunoadsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates, therefore, a method for detecting an aberrant GM-CSF or GM-CSFR or for determining whether a GM-CSF or GM-CSFR is a variant in a biological sample from a subject, said method comprising contacting said biological sample with an antibody specific for said GM-CSF or GM-CSFR or a component thereof or its derivatives or homologs or higher order forms for a time and under conditions sufficient for an antibody-polypeptide complex to form, and then detecting said complex.

A biological sample includes a cell extract.

Immunoassays may be conducted in a number of ways such as by Western blotting and ELISA procedures. A wide range of immunoassay techniques are available as can be seen by reference to U.S. Pat. Nos. 4,016,043, 4,424,279 and 4,018,653.

Sandwich assays are among the most useful and commonly used assays and are favored for use in the present invention. A number of variations of the sandwich assay technique exist, and all are intended to be encompassed by the present invention. Briefly, in a typical forward assay, an unlabeled antibody is immobilized on a solid substrate and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labeled antibody are added simultaneously to the bound antibody. These techniques are well known to those skilled in the art, including any minor variations as will be readily apparent. In accordance with the present invention the sample is one which contains a GM-CSF/GM-CSFR complex or particular form thereof or a component thereof.

In the typical forward sandwich assay, a first antibody having specificity for the present cytokine or receptor or antigenic parts thereof or higher order forms thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or where more convenient, overnight) and under suitable conditions (e.g. for about 20° C. to about 40° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labeled with a reporter molecule. Depending on the amount of target and the strength of the reporter molecule signal, a bound target may be detectable by direct labelling with the antibody. Alternatively, a second labeled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic colour visually detectable with a light microscope. The fluorescent labeled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescence and EIA techniques are both very well established in the art and are particularly preferred for the present method. However, other reporter molecules, such as radioisotope, chemi-luminescent or bioluminescent molecules, may also be employed.

In another aspect, the present invention provides a composition, e.g, a pharmaceutical composition, containing one or a combination of monoclonal antibodies of the present invention or small molecule antagonists or agonists of one of Sites 1 through 4, formulated together with at least one additional component. Such compositions may include one or a combination of (e.g, two or more different) antibodies, or immunoconjugates or bispecific molecules of the invention. For example, a pharmaceutical composition of the invention can comprise a combination of antibodies (or immunoconjugates or bispecifics or other agents) that bind to different epitopes on the target antigen or that have complementary activities.

Thus, pharmaceutical compositions according to the present invention, and for use in accordance with the present invention, may comprise, in addition to active ingredient, pharmaceutically acceptable carriers, diluents and/or excipients. The precise nature of the carrier or other material will depend on the route of administration, which may be oral, or by injection, e.g. intravenous.

Pharmaceutically acceptable carriers, diluents and/or excipients include any and all solvents, dispersion media, coatings, antibacterial and antifungal agents, agents used for adjusting tonicity, buffers, chelating agents, and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of micro-organisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thimerosal and the like. In many cases, it will be preferable to include agents to adjust tonicity, for example, sugars or sodium chloride. Prolonged absorption of the injectable compositions can be brought about by the use in the compositions of agents delaying absorption, for example, aluminium monostearate and gelatin. The compositions may also include buffers and chelating agents.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

The amount of active compound in such therapeutically useful compositions is such that a suitable dosage will be obtained.

Dosage regimens are adjusted to provide the optimum desired response (e.g, a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, or once a month.

In some methods, two or more monoclonal antibodies with different binding specificities are administered simultaneously, in which case the dosage of each antibody administered falls within the ranges indicated.

Alternatively, antibody can be administered as a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the present invention include intravenous, intramuscular, intradermal, intraperitoneal, subcutaneous or other parenteral routes of administration, for example by infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g, *Sustained and Controlled Release Drug Delivery Systems*, Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556.

The terms "compound", "active agent", "chemical agent", "pharmacologically active agent", "medicament", "active" and "drug" are used interchangeably herein to refer to a chemical compound that induces a desired pharmacological and/or physiological effect and identified or designed based on the atomic coordinates listed in Table 1 or a biological assay or both. The terms also encompass pharmaceutically acceptable and pharmacologically active ingredients of those active agents specifically mentioned herein including but not limited to salts, esters, amides, prodrugs, active metabolites, analogs and the like. When the terms "compound", "active agent", "chemical agent" "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc. Such components are proposed to be useful as medicaments for the treatment of a range of pathologies such as cancer including leukemia, immune-based conditions, cardiovascular disease, ischemia, brain and heart infarcts, inflammatory conditions and infection by pathogenic agents. Reference to leukemia includes a cytokine-dependent (e.g. GM-CSF or IL-3) leukemia.

Examples of cancers contemplated herein includes solid and blood borne cancers, leukemias, sarcomas and carcinomas. Examples of cancers which may be treated using the protocol of the present invention include but are not limited to ABL1 protooncogene, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynacological cancers, hematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, li-fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer (NMSC), non-small-cell-lung-cancer-(NCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia or Wilms' tumor.

Reference to a "compound", "active agent", "chemical agent" "pharmacologically active agent", "medicament", "active" and "drug" includes combinations of two or more actives. A "combination" also includes multi-part such as a two-part composition where the agents are provided separately and given or dispensed separately or admixed together prior to dispensation.

For example, a multi-part pharmaceutical pack may have two or more agents identified using the atomic coordinates of Table 1 separately maintained. A pharmaceutical pack includes a kit. A kit may contain antibodies, agents, software containing the atomic coordinates amongst other components.

The terms "effective amount" and "therapeutically effective amount" of an agent as used herein mean a sufficient amount of the agent to provide the desired therapeutic or physiological effect or outcome. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

The agents may be formulated in a composition further comprising a pharmaceutical acceptable carrier, excipient or diluent.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, emide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms of the condition being treated, elimination of symptoms and/or underlying cause, prevention of the occurrence of symptoms of the condition and/or their underlying cause and improvement or remediation or amelioration of damage following a condition.

"Treating" a subject may involve prevention of a condition or other adverse physiological event in a susceptible individual as well as treatment of a clinically symptomatic individual by ameliorating the symptoms of the condition.

A "subject" as used herein refers to an animal, preferably a mammal and more preferably human who can benefit from the pharmaceutical formulations and methods of the present invention. There is no limitation on the type of animal that could benefit from the presently described pharmaceutical formulations and methods. A subject regardless of whether a human or non-human animal may be referred to as an individual, patient, animal, host or recipient. The compounds and methods of the present invention have applications in human medicine, veterinary medicine as well as in general, domestic or wild animal husbandry.

As indicated above, the preferred animals are humans or other primates such as orangutangs, gorillas, marmosets, livestock animals, laboratory test animals, companion animals or captive wild animals, as well as avian species.

Examples of laboratory test animals include mice, rats, rabbits, guinea pigs and hamsters. Rabbits and rodent animals, such as rats and mice, provide a convenient test system or animal model. Livestock animals include sheep, cows, pigs, goats, horses and donkeys. Non-mammalian animals such as avian species, zebrafish, and amphibians including *Xenopus* spp.

The present invention further provides animal model systems to test potential agonists or antagonists of Sites 1 through 4. In one embodiment, the animal model or primate genetically engineered to express human GM-CSF and/or GM-CSFR or a component thereof. The animal model may further comprise a knock out in its indigenous GM-CSF or GM-CSFR genetic material. Reference to "GM-CSFR" in this context includes one or both of the α-chain and/or βc chain.

The preferred crystal structure is in relation to human GM-CSF/GM-CSFR. However, crystal structures of GM-CSF/GM-CSFR from other animal species are encompassed by the present invention.

The following examples illustrate various aspects of this invention. This invention is not to be limited in scope by the specific embodiments described below. Indeed various modifications of the invention in addition to those described herein will become apparent to those skilled in the art from the foregoing description. Such modifications are intended to fall within the scope of the appended claims. The disclosures of patents, patent applications and publications cited herein are incorporated by reference in their entireties.

In these Examples, materials and methods as outlined below are employed.

Expression and Purification of Receptor Components

Soluble human GM-CSF (SEQ ID No. 16) was produced in *Escherichia coli* and purified by anion exchange chromatography and reversed phase HPLC (Hercus et al, Proc. Natl. Acad. Sci. USA 91:5838, 1994). DNA fragments encoding the soluble extracellular domains of GM-CSFRα (sGM-CSFR α; (SEQ ID No. 17) or βc (sβc; (SEQ ID No. 18) were cloned into the pIBV5-His expression vector (Invitrogen, Australia) and transfected into Sf21 insect cells using Cellfectin (Invitrogen, Australia). Permanently transfected Sf21 cell lines were selected for by incubation with Blasticidin at 50 μg/ml (Invitrogen, Australia) but once established Blasticidin treatment was discontinued. Sf21 cells and transfected cell lines were maintained in serum-free ExCell 420 medium (JRH Biosciences, Australia) at 27° C. Large-scale expression generated up to 40 L of conditioned medium which was concentrated to less than 1 L prior to affinity chromatography as previously described (McClure et al, Blood 101:1308, 2003).

Human βc contains three N-linked glycosylation sites and elimination of the third site at $Asn^{346}$ by glutamine substitution has previously been demonstrated to improve the diffraction properties of crystallized sβc (Carr et al, supra 2001). Full-length βc N346Q retains wild-type function when co-transfected with full-length GM-CSFRα in GM-CSF receptor binding assays using transiently transfected COS cells. sβc N346Q was expressed and purified from an Sf21 cell line and displayed a modest reduction in molecular weight compared to the wild-type sβc but no difference in its ability to form a ternary complex with sGM-CSFRα and GMCSF.

Crystallization of the Complex

Ternary complex consisting of GM-CSF of SEQ ID NO:16, sGM-CSFRα of SEQ ID NO:17 and sβc N346Q of SEQ ID NO:18 was isolated by gel filtration chromatography using a Superdex 200 column (26-mm×600 mm, GE Healthcare, Australia) operated at 2 ml/min at 4° C. with 150 mM NaCl, 50 mM sodium phosphate pH 7.0, as running buffer. A number of crystal forms of the wild-type ternary complex were grown but none diffracted beyond 8 Å resolution using synchrotron radiation. A number of crystal forms of the ternary complexes were grown using the sβc N346Q of SEQ ID NO:18° construct. However, only one out every 100 crystals diffracted beyond 4 Å resolution. Briefly, using the hanging drop technique crystals appeared after 1 week and grew to full size (up to 0.8×0.8×0.4 mm) within 2 weeks. The best crystal was obtained mixing 1 μl of ternary GM-CSF receptor complex at a concentration of ~5 mg/ml with 1 μl reservoir solution containing 100 mM HEPES buffer pH 7.0, 6% (v/v) PEG3350, 0.2M proline at 20° C. The crystal belonged to the space group P6322 with unit cell dimensions a=b=166.6 Å and c=213.1 Å.

Structure Determination of the Complex

Diffraction data were collected at 100 K and recorded on an ADSC Quantum-315 CCD detector on BioCARS beam line 14-BM-C at the Advanced Photon Source (Chicago, USA). The wavelength was set to 0.9 Å. Data were processed using the methods described in Table 5. The best crystal diffracted to a resolution of 3.3 Å. The structure was determined by molecular replacement using the method of Storoni et al, *Acta Crystallogr. D* 60:432, 2004. The search models were GM-CSF βc chain (PDB id: 1 GH7; (Can et al, supra 2001)) and GM-CSF (PDB id: 2GMF; (Rozwarski et al, *Proteins* 26:304, 1996)).

Molecular replacement solutions for GM-CSF βc and GM-CSF gave Z-scores of 51.6 and 6.3 to a resolution of 3.3 Å, respectively. Difference electron density maps calculated with phases obtained after a few rounds of refinement clearly showed unexplained density close to domain 4 of the βc chain. A homology model of domain 2 of the alpha chain was built into this density. (The choice of which alpha chain domain to build into the density was straight forward as it was interacting with domain 4 of βc, the membrane proximal domain of that chain, and thus the correct choice had to be the membrane proximal alpha chain domain 2.) The model was completed by iterative cycles of manual rebuilding using the method of *Acta Crystallogr. D Biol. Crystallogr.* 50:760, 1994 and refinement using the method of Murshudov et al, *Acta Crystallogr. D* 53:240, 1997. In the final refinement steps the βc model was replaced by a better quality structure that just became available (PDB id: 2GYS; (Can et al, supra 2006)). During the final refinement step each subunit was treated as a rigid body for the purposes of TLS (translation, libration and screw rotation tensors) refinement to account for overall differences in displacements between the molecules and anisotropy in the data (Winn et al, *Acta Crystallogr. D* 57:122, 2001; Painter and Merritt, *Acta Crystallogr. D* 62:439, 2006). Despite the low resolution of our data, the availability of refined structures of two of the components (βc dimer (2.7 Å resolution) (Can et al, supra 2006); GM-CSF (2.4 Å resolution) (Rozwarski et al, supra 1996), combined with rigidity of the structural modules (<1.75 Å rmsds from their unliganded structures), suggests a more accurate model than the resolution would indicate. For example, electron density corresponding to the F-G loop in domain 4 of βc, which includes the essential residue $Tyr^{421}$, indicated a different conformation of this loop from that described in the original structure of βc (Can et al, supra 2001), although the initial maps were calculated using this model.

TABLE 5

Data collection and refinement statistics

| | CM-CSF Receptor Complex |
|---|---|
| Data collection | |
| Space group | P6$_3$22 |
| Cell dimensions | |
| a, b, c (Å) | 166.6, 166.6, 213.1 |
| α, β, γ (°) | 90, 90, 120 |
| Resolution (Å) | 3.3 (3.5-3.3) |
| $R_{merge}$ | 7.7 (62.1) |
| I/σI | 17.7 (2.3) |
| Completeness (%) | 99.7 (99.7) |
| Redundancy | 4.7 (4.8) |
| Refinement | |
| Resolution (Å) | 3.3 |
| No. reflections | 25,439 |
| $R_{work}/R_{free}$ (%) | 27.0/31.7 |
| No. atoms | 5127 |
| B-factors after TLS refn (Å) | |
| All atoms | 122.7 |
| GM-CSF-alpha | 126.3 |
| GM-CSF-beta | 122.2 |
| GM-CSF | 120.8 |
| r.m.s. deviations | |
| Bond lengths (Å) | 0.013 |
| Bond angles (°) | 1.5 |

The final model includes residues 25-436 of βc. The sequence of the published structure of βc, a variant of the one used in this work, has a six residue insertion in the C-D loop of domain 3. Density for parts of this loop were not observed in the published structure (Carr et al, supra 2006) but is well defined in the complex. Additionally, several loops including residues 157 to 161 (B-C loop of domain 1 in both chains), residues 349 to 351 (A-B loop in domain 4, chain A) and residues 361 to 368 (B-C loop in domain 4, chain A) were missing in the published structure but are well defined in our model. As observed in the apo structure of βc, two carbohydrate chains are covalently linked to $Asn^{58}$ (built as NAG-NAG-MAN) and $Asn^{191}$ (built as NAG). The model of GM-CSF starts at residue 14 and ends at residue 118. Although electron density for GM-CSFRα is generally weaker in comparison to the rest of the structure, large parts of domain 2 could be traced (residues 218-316) including a portion of a carbohydrate chain covalently linked to $Asn^{229}$ (modeled as NAG-NAG). In general the main chain of GM-CSFRα in this region is well defined by electron density. Density modification, sharpening of structure factors and calculation of composite omit maps did not lead to any significant improvement of electron density maps. Although the electron density for N-terminal FnIII domain (GM-CSFRα domain 1) is of poorer quality, it was sufficient to build a partial polyalanine model including a two-stranded beta-sheet. A homology model of the complete GM-CSFRα domain 1 could be superimposed onto the partial structure. SDS-PAGE gels of washed crystals confirm that all three domains of GM-CSFRα are present indicating the N-terminal knob domain is disordered in the crystals. The stereochemical quality of the final model correlates well with structures at similar resolutions with 96.8% residues in the allowed regions of the Ramachandran plot and only 18 residues in the disallowed regions. Other stereochemical parameters are all better than or within the allowed ranges defined by PROCHECK.

Receptor Binding Assay

Mutations of βc were generated by site-directed mutagenesis using the Altered site system (Promega, Australia) and along with wild type βc cDNAs, sub-cloned into the pcDNA1 expression vector (Invitrogen, Australia) as previously described (Woodcock et al, *J. Biol. Chem.* 271:25999, 1996). The GM-CSFRα and IL-3Rα cDNAs were cloned into the pCDM8 expression vector (Invitrogen, Australia) (Woodcock et al, supra 1996). COS cells were co-transfected with GM-CSF and IL-3 receptor a chain together with mutant or wild type β chains by electroporation and cell surface expression was confirmed by indirect immuno-fluorescence staining as previously described (Woodcock et al, supra 1996).

Receptor saturation binding assays with radio-iodinated IL-3 and GM-CSF were carried out on transfected COS cells adhered to 24 well plates 2-3 days after transfection (Woodcock et al, supra 1996). Dissociation constants were determined using the EBDA and LIGAND programs (Biosoft, Cambridge, United Kingdom) (Munson and Rodbard, *Anal. Biochem.* 107:220, 1980).

Cell Lines and Proliferation Assays

Mutant and wild type βc cDNAs were cloned into the expression vector pRcCMVpuro which is based on pRcCMV (Invitrogen) in which the Neomycin resistance cassette has been replaced with the Puromycin resistance cassette (Jenkins and Gonda, *J. Biol. Chem.* 274:8669, 1999). CTL-EN cells stably expressing hIL-3 receptor a chain (CTL-EN/IL3Rα, were grown routinely in DMEM supplemented with 10% v/v FCS, 2 mM glutamine, 50 µM 2-mercaptoethanol and 100 U/ml mIL-2. CTL-EN/hIL-3Rα cells ($2\times10^6$) were electroporated with 10 µg of pRcCMVpuro DNA encoding wild-type or Site 2 mutant βc at 960 µF with 270V and selected in 2 µg/ml puromycin 48 hours after transfection. Selected lines were subsequently transduced with a retrovirus encoding GM-CSFRα cDNA essentially as described previously (Jenkins et al, supra 1996). CTL-EN cells ($5\times10^6$) stably expressing hIL-3 receptor a chain and human GM-CSF receptor a chain (CTL-EN/IL3Rα/GMRα), were grown routinely in RPMI supplemented with 10% v/v FCS, 2 mM glutamine, 50 µM 2-mercaptoethanol and 100 U/ml mL-2. CTL-EN/IL3Rα/GMRα cells were electroporated with 20 µg of pRcCMVpuro DNA encoding wild-type or Site 4 mutant βc and puromycin resistant cell lines selected as described above.

CTL-EN cell lines were starved of mIL-2 overnight and incubated ($1\times10^4$ cells per well) with growth factors over a range of concentrations for 48 hours. The cells were then pulsed with 0.5 µCi [$^3$H]-thymidine per well for four hours prior to harvesting onto glass fibre filter mats and the cell-associated radioactivity was determined by scintillation counting. Alternatively, cells were pulsed with MTS (Promega, Madison, Wis.) and after 4 hours at 37° C., the absorbance at 490 nm was recorded using an ELISA plate reader.

Biochemical Analysis of βc Receptor Function

CTL-EN(CTL-EN/IL3Rα/GMRα) cell lines stably expressing wild type βc or M7-βc were starved of mIL-2 in medium containing 0.5% v/v FCS at 37° C. overnight and then stimulated for 5 min at 37° C. with GM-CSF or IL-3. Cells were lysed, $β_c$ immunoprecipitated and the precipitates subjected to immunoblot analysis with anti-phospho-tyrosine (4G10) or anti-$β_c$ (1C1) antibodies (Woodcock et al, supra 1996). Cell lysates were also subjected to SDS-PAGE and immunoblotted with anti-phospho-JAK2, and anti-phospho-STAT5 antibodies.

Size Exclusion Chromatography

Purified sβc ΔN3 was titrated (1.1-10.7 µM) alone or mixed with equimolar sGM-CSFRα and a 1.5× molar excess of GM-CSF, adjusted to 50 µl with 150 mM NaCl, 50 mM sodium phosphate pH7 and incubated at 25° C. for at least one hour. Samples were chromatographed on a SMART system using a Superdex 200PC column (3.2 mm×300 mm, GE Healthcare, Australia) as previously described (McClure et al, supra 2003). Elution time and area of eluted peaks was determined using the instruments software.

Generation of a Monoclonal Antibody to the Site of Dodecamer Formation on the Human Beta Common Chain 1. Cell Culture FreeStyle™ 293-F cells and the mammalian expression vector pcDNA3.1 are obtained from Invitrogen. Cells are cultured in FreeStyle™ Expression Medium (Invitrogen). Balb/c 3T3 fibroblasts are obtained from ATCC and are cultured in RPMI 1640 (Invitrogen) supplemented with 15% v/v fetal bovine serum (Sigma-Aldrich). Sp2/0 cells are obtained from ATCC and are cultured in RPMI 1640 (Invitrogen) supplemented with 10% v/v fetal bovine serum (Sigma-Aldrich). All tissue culture media is supplemented with penicillin/streptomycin/fungizone reagent (Invitrogen) and cells are maintained at 37° C. in humidified incubators with an atmosphere of 8% v/v $CO_2$.

2. Transient Transfections for Generation of Immunization and Screening Antigens Transient transfections of expression plasmids encoding soluble human beta common chain and membrane bound human beta common chain and variants using FreeStyle™ 293-F cells is performed using 293fectin transfection reagent (Invitrogen) according to the manufacturer's instructions.

Transient transfections into Balb/c 3T3 cells of expression plasmids encoding membrane-bound wild type human beta common chain is accomplished using a Nucleofector (Amaxa) with Nucleofector Kit V according to the manufacturer's instructions.

3. Generation of cDNA Expression Plasmids Encoding the Human Beta Common Chain and Variants A synthetic gene encoding the wild type human beta common chain protein and variants of the human beta common chain are constructed by Geneart AG (Regensburg, Germany). A Kozak sequence is introduced just before the N-terminus of each protein to increase translational initiation. A 6×His sequence is added in-frame at the C-termini of the wild type human beta common chain and variant proteins to enable either detection by Western blot analysis using an anti-6×His antibody or purification of soluble proteins by Nickel affinity chromatography. Two stop codons are added after the 6×His-tag to ensure efficient translational termination. The codon usage of the wild type human beta common chain cDNA is adapted to the codon bias of *Homo sapiens* genes. The M1 variant of the human beta common chain contains the following changes: 347VTKDG351 to 347AAAAA351 to disrupt domain 4 of human beta common A strand. The M7 variant of the human beta common chain contains residues 430 to 435 (strand G of human beta common domain 4) substituted with poly-alanine to disrupt Site 4. An Nhe I restriction site at the 5' end of the cDNA and a Xho I restriction site is introduced at the 3' end in order to ligate the Geneart cDNAs into Nhe I-Xho I digested pcDNA3.1.

The cDNAs encoding the extracellular domain of the wild-type human beta common chain and the full-length amino acid sequence of the human beta common chain M1 and M7 variants are constructed using standard PCR procedures (Heckman and Pease, *Nature Protocols* 2:924-932, 2007) with Accuprime Pfx DNA Polymerase (Invitrogen) according to the manufacturer's instructions. Once each cDNA is complete, it is digested with Nhe I and Xho I and ligated into pcDNA3.1. Large-scale preparations of plasmid DNA are carried out using a Qiagen Maxi Kit according to the manufacturer's instructions. The nucleotide sequences of all the plasmid constructs are verified by sequencing both strands using Big Dye Terminator v3.1 Cycle Sequencing and an Applied Biosystems Automated Sequencer.

4. Analysis of Protein Expression and Purification of the Soluble Extracellular Domains of Wildtype Human Beta Common Chain After five days 20 µl of culture supernatant from a transfection of the expression construct encoding the wildtype soluble human beta common chain is electrophoresed on a 4-20% v/v Tris-Glycine SDS polyacrylamide gel and the protein is visualised by staining with Coomassie Blue reagent. The cell culture supernatant containing soluble human beta common chain protein is harvested by centrifugation at 2500 rpm and passed through a 0.45 µM filter (Nalgene) prior to purification. 6×His-tagged wildtype human beta common chain protein is purified on Qiagen Ni-NTA Superflow Columns according to the manufacturer's instructions.

5. Flow Cytometry Staining

For flow cytometry staining's, FreeStyle™ 293-F cells are transfected as described above with expression constructs encoding either full-length wild-type human beta common chain or human beta common M1 or M7 variants. Once transfected, the cells are cultured for 48 hours. Staining's ($5\times10^5$ transfected FreeStyle™ 293-F cells) are performed in round-bottomed 96-well plates for 20 minutes on ice with 500 hybridoma fusion supernatant followed by PE-coupled goat anti-mouse IgG (Jackson Immunoresearch Laboratories). The cells are analysed on a BD Biosciences flow cytometer using the CellQuest program.

6. Immunization, Cell Fusion and Screening

Monoclonal antibodies are produced essentially as previously described (Goding, *Monoclonal Antibodies: Principles and Practice* $2^{nd}$ *Ed., New York: Academic*, 1986). Six-week old female Balb/c mice are immunized intra-peritoneally with either $10^6$ cells expressing membrane-bound human beta common chain or 50 µg soluble human beta common chain in the presence of complete Freund's adjuvant. The mice receive two additional boosts with the same amounts of antigen in incomplete Freund's adjuvant (Sigma-Aldrich) at 3-week intervals. Three days before the fusion and 3 weeks after the previous boost mice receive a final boost (50 µg soluble human beta common chain or $10^6$ Balb/c 3T3 cells expressing membrane-bound human beta common chain in PBS) administered by tail vein injection and intra-peritoneally. Hybridomas are generated following fusion of hypoxanthine/aminopterin/thymidine (HAT)-sensitive Sp2/0 myeloma cells with splenocytes from immunized Balb/c mice. Ten days after the fusion, hybridoma supernatants are screened by ELISA for antibodies to the wild-type human beta common chain in 96-well plates. Clones from wells that are positive to wild-type human beta common are re-screened using flow cytometry for binding to the wild-type human beta common chain and either the M1 or M7 variants of the human beta common chain. Clones from wells positive to wild-type human beta common chain that are negative to either of the variants are sub-cloned by limit dilution and monoclonal antibodies are produced by standard tissue culture procedures in CD-Hybridoma medium (Invitrogen). Isotyping is determined using a Mouse Monoclonal Antibody Isotyping Kit according to the manufacturer's instructions (Amersham). IgG is isolated from culture supernatant by Sepharose Protein G affinity chromatography according to the manufacturer's instructions (Amersham).

7. Inhibition of IL-3-mediated TF-1 Cell Proliferation.

Tests for the biologic activity of antibody preparations are performed using the TF-1.8 cell proliferation assay essentially as described (Kitamura et al, *J. Cell Physiol.* 140:323-34, 1989). Briefly, TF-1.8 cells (Sun et al, *Blood,* 94:1943-1951, 1999) are GM-CSF-starved for 24 hours before setting up proliferation assays. $1\times10^4$ cells are incubated with 0.3 ng/mL IL-3 in culture media the presence of a range of concentrations of mAbs (100 µg/to 0.0001 µg/mL) for 48 hours at 37° C. in 96 well microtitre plates at a volume of 200 µL/well. Wells are pulsed with 1 µCi per well $^3$H-thymidine for the final 6 hours. The cells are harvested onto glass fibre filters and the $^3$H-thymidine incorporated into DNA is determined by liquid scintillation counting and expressed as counts per minute (cpm). Beta common receptor neutralizing activity is assessed as the inhibition of proliferation measured as decreased $^3$H-thymidine incorporation into cellular DNA in response to IL-3, GM-CSF and IL-5. Antibody potency is quantified as the dose mediating a 50% inhibition of the proliferative response ($ED_{50}$) to cytokine.

Example 1

Atomic Coordinates of GM-CSF/GM-CSFR Complex

The atomic coordinates of the human GM-CSF/GM-CSFR crystalline complex are set forth in Table 1 (SEQ ID No. 15).

Lengthy table referenced here

US08489339-20130716-T00001

Please refer to the end of the specification for access instructions.

Example 2

Determination of Crystal Structure of GM-CSF/GM-CSFR Ternary Complex

Figure 5:
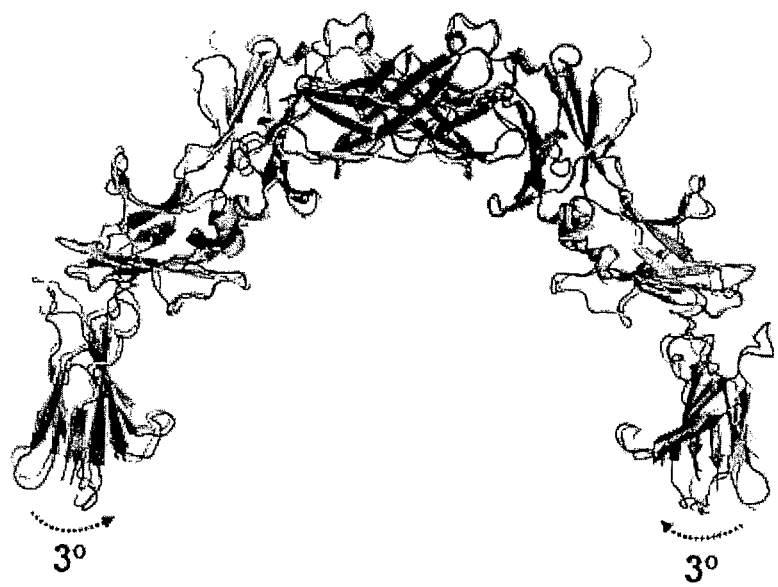

The crystal structure of the GM-CSF/GM-CSFR ternary complex is determined revealing a 2:2:2 hexamer consisting of two βc chains, two GM-CSFRα chains and two GM-CSF molecules (FIG. 1). The atomic coordinates are listed in Table 1 (Example 1). The structure adopted by GM-CSF in the ternary complex is similar to the structure of the isolated GM-CSF (Rozwarski et al, supra 1996). The same intertwined βc homodimer previously seen in the structure of the isolated βc subunit is also observed (Can et al, supra 2001). In the present case, the dimer is generated by a crystallographic twofold axis which runs through the center of the hexameric complex. Each βc chain consists of two cytokine receptor homology modules (CRMs), each of which consists of two fibronectin type III (FnIII) domains. A comparison of the βc chain in the complex compared to the published structure of the isolated molecule reveals that domain 4 has rotated 3° towards the crystallographic diad (FIG. 5). The hinge region about which the rotation has occurred is located close to domain 1 in the linker region connecting domains 3 and 4 although the conformation of the linker region closely resembles that seen in the isolated molecule. The GM-CSFRα chain consists of an N-terminal. "knob" domain followed by one CRM. However, we only observe good electron density for the C-terminal FnIII domain of GM-CSFRα (GM-CSFRα domain 2).

Analysis of ternary complex formation at high protein concentrations (~10 µM) demonstrated complexes with a higher MWt (FIG. 6), consistent with a 2:2:2 stoichiometry. The analogous IL-6 receptor system also exists as either a 2:1:1 complex (2 gp130 (equivalent to βc): 1 IL-6R α: 1 IL-6) or a 2:2:2 complex. The differences in the models may reflect a mechanism by which complex receptor systems can respond to differing cytokine concentrations.

Figure 2:
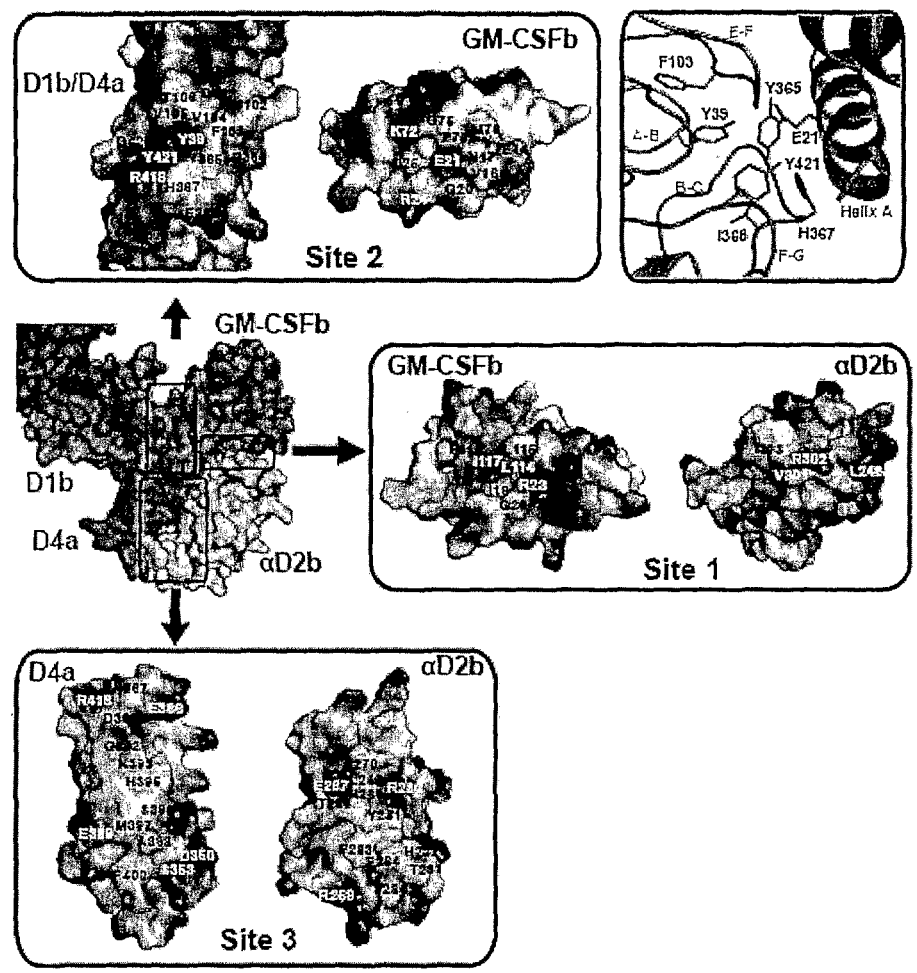
Figure 7:
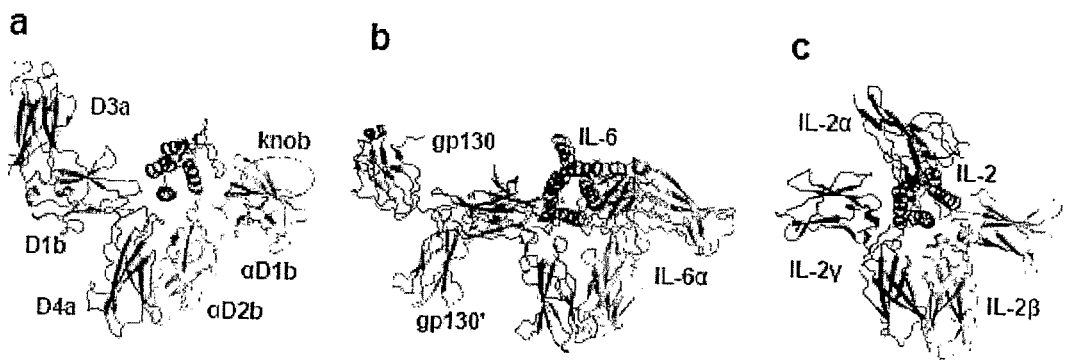

Only broken density is observed for domain 1 of GM-CSFR α and hence its location is modeled using the structure of the IL-2 beta chain (Wang et al, *Science* 310:1159, 2005) as a guide (FIG. 7). Although the electron density for N-terminal FnIII domain (GM-CSFR α domain 1) is of poorer quality, it was sufficient to recognise core β-sheet enabling a partial model to be built and refined. GM-CSF binds to the elbow region defined by domains 1 and 2 of GM-CSFRα, reminiscent of the binding mode seen in other class I cytokine receptors (FIG. 7) (Wells and de Vos, *Annu. Rev. Biochem.* 65:609, 1996). There is a small interaction surface between GM-CSF and GM-CSFRα domain 2 of ~240 Å$^2$ per molecule with a surface complementarity of 0.66, a value within the range of normal protein-protein interaction surfaces (FIG. 2, Site 1). Additional surface area would be provided by domain 1. The loop residues 241 to 251 and 299 to 305 of GM-CSFRα interact with residues 11 to 23 (Helix A) and residues 112 to 118 (Helix D) of the cytokine.

Recruitment of βc to the GM-CSF:GM-CSFRα binary complex converts the GM-CSF binding to high affinity and leads to receptor activation. Our structure reveals a GM-CSF binding site at the elbow region between domain 1 (A-B and E-F loops) of one βc chain and domain 4 (B-C and F-G loops) of the second βc chain (FIG. 2, Site 2), consistent with previous mutagenesis data. The interaction at Site 2 buries ~570 Å$^2$ of surface area per molecule with a surface complementarity value of 0.62. Helix A of GM-CSF nestles into a surface crevice of βc formed by the E-F loop (residues 100 to 107) of βc domain 1 and the B-C (residues 360 to 369) and F-G (residues 417 to 423) loops of domain 4 (FIG. 2, Site 2). All the loops of βc that interact with cytokine adopt conformations very similar to that seen in isolated βc. In βc domain 1, Tyr$^{39}$ of the A-B loop could form pi-pi interactions with Tyr$^{421}$ in the F-G loop of domain 4. Residues Val$^{104}$, Val$^{105}$ and Thr$^{106}$ of the E-F loop of domain 1 nestle into a hydrophobic pocket formed by helices A and C of GM-CSF. The side chain of the adjacent Phe$^{103}$ residue is sandwiched between E-F and A-B loops of domain 1 stabilizing the conformation of this region in the Site 2 interface. Asp$^{107}$ potentially forms a salt bridge interaction with Lys$^{72}$ of GM-CSF. Tyr$^{365}$ and His$^{367}$ of the B-C loop of domain 4 are positioned on either side of Glu$^{21}$ of GM-CSF. In the F-G loop of βc domain 4, Tyr$^{421}$ potentially interacts with Glu$^{21}$ of GM-CSF.

Mutagenesis studies of βc confirm the nature and functional significance of the observed interactions. Loss of the phenolic hydroxyl at Tyr$^{39}$ by phenylalanine substitution does not affect GM-CSF high-affinity binding whereas alanine substitution of either Tyr$^{39}$ or Phe$^{103}$ completely abolishes GM-CSF high-affinity binding (Murphy et al, supra 2003; Murphy et al, *J. Biol. Chem.* 279:26500, 2004). Loss of the phenolic hydroxyl at Tyr$^{365}$ by phenylalanine substitution does not affect GM-CSF high-affinity binding (Lock et al, *Proc. Natl. Acad. Sci. USA* 91:252, 1994) whereas alanine substitution at Tyr$^{365}$, His$^{367}$ or Ile$^{368}$ abolishes GM-CSF binding (Woodcock et al, *EMBO J.* 13:5176, 1994). Ablation of high-affinity GM-CSF binding with the βc Y421F mutant (FIG. 3A) highlights the importance of the phenolic hydroxyl group in ligand binding while a lack of additional interactions within the F-G loop is consistent with previous scanning mutagenesis work (Woodcock et al, supra 1994

The principal cytokine interaction with βc occurs through a conserved glutamate in helix A of GM-CSF (Glu$^{21}$), IL-3 (Glu$^{22}$) or IL-5 (Glu$^{13}$). We have demonstrated that Glu$^{21}$ of GM-CSF is essential for high-affinity binding and function of GM-CSF (Hercus et al, supra 1994) as well as the direct physical association of GM-CSF with βc (McClure et al, *Blood* 101:1308, 2003). No other βc contact residues in helix A of GM-CSF appear to be essential for function (Hercus et al, *Blood* 83:3500, 1994).

Domain 2 of GM-CSFRα forms an extensive interaction with domain 4 of βc resulting in ~680 Å$^2$ of buried surface area per molecule with a surface complementary value of 0.52. The interface, involving residues 231, 232, 259, 266-270 and 280-286 of GM-CSFRα and residues 350, 353, 366-369, 389-400 and 418 of βc, is predominantly hydrophobic with a rim of charged residues (FIG. 2, Site 3). Two surface hydrophobic patches have been reported, denoted H1 and H2, in the crystal structure of βc domain 4 and it has been speculated they might be involved in interaction with other parts of βc and GM-CSFRα, respectively (Rossjohn et al, supra 2000). The structure here shows that residues in H1 contact the A-B loop of βc domain 1 whereas residues of H2, located at the edge of the beta strands D and E of βc domain 4, are involved in the formation of the interface with GM-CSFRα. The Site 3 interface provides additional interacting surfaces between GM-CSFRα and βc thereby enhancing the overall binding affinity of GM-CSF for its receptor.

The crystal lattice generates an unexpected dodecamer complex consisting of two hexameric complexes related by a crystallographic twofold axis (FIG. 4A). Intriguingly, the dodecamer assembles in a head-to-head orientation bringing the C-terminal tails of neighboring βc domain 4's and GM-CSFRα domain 2's into close proximity suggesting a physiological relevance to the assembly (FIG. 4B). The interaction surface is large with ~770 Å$^2$ being buried per hexamer with major contributions between βc domain 4 of each hexamer (~520 Å$^2$ per molecule) and the rest contributed from an interaction between the GM-CSFRα of one hexamer and βc domain 4 of the other. The mostly polar interface involves residues 260 and 261 of GM-CSFRα and residues 346-354, 357, 359, 362, and 430-435 of βc with a high surface complementarity value of 0.63. The βc domain 4 dodecamer interface includes the mutated N-linked glycosylation site, N346Q. Modeling two N-acetylglucosamine residues at this site shows that glycosylation is readily accommodated, increasing the contact area at the interface and potentially modulating signaling.

Figure 4:
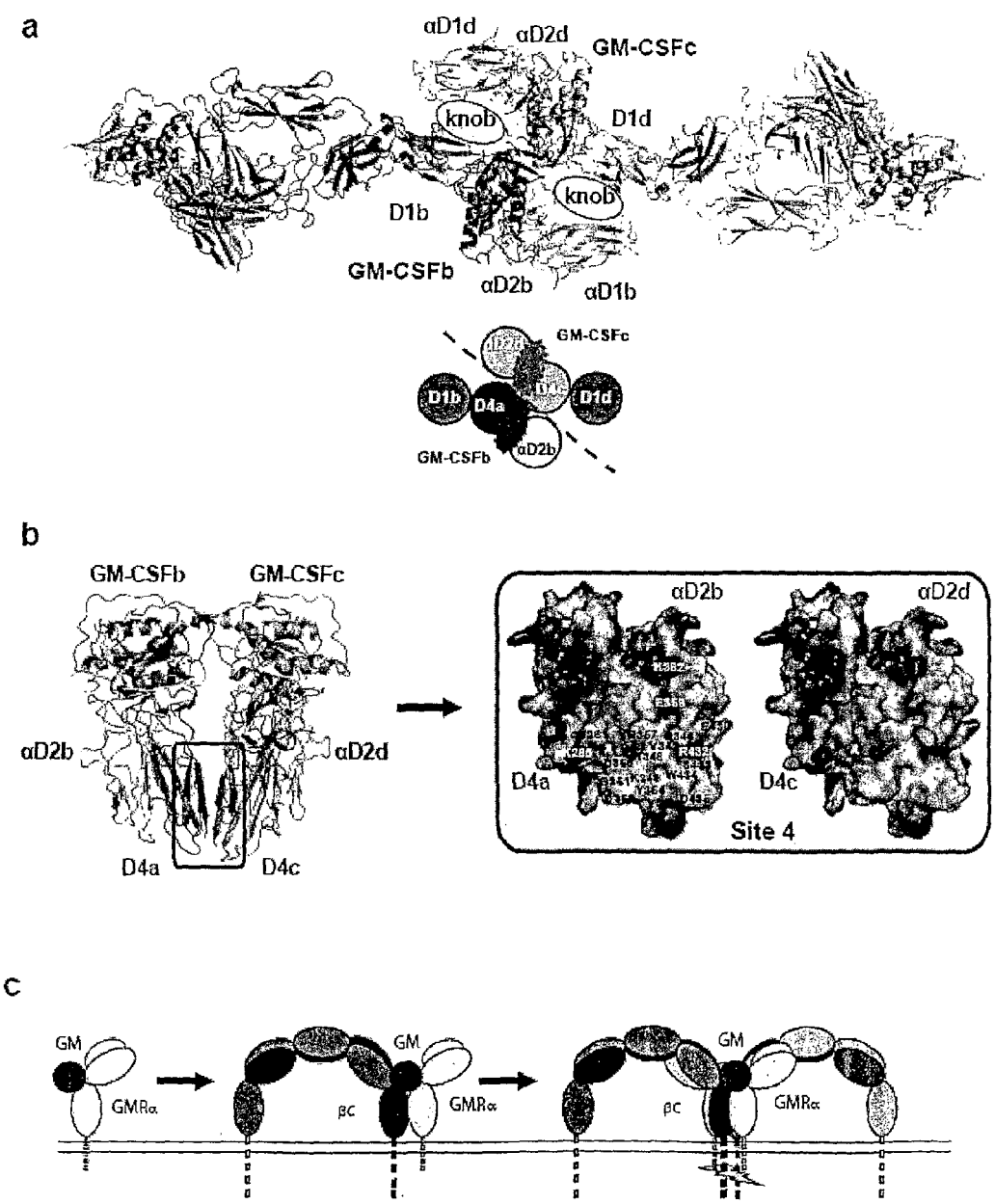

Several lines of evidence have shown that GM-CSF receptor activation requires the participation and proximity of at least two βc and two GM-CSFRα cytoplasmic domains (Lia et al, *J. Biol. Chem.* 271:28287, 1996; Muto et al, *Biochem. Biophys. Res. Commun.* 208:368, 1995). A surprising feature of the published βc dimer structure was that the cytoplasmic tails were ~120 Å apart raising the question of how signaling could occur. Similarly in our hexameric complex there are two alpha subunits (FIG. 1) but they are located too far apart to participate in receptor activation. A striking feature of the dodecamer structure is that the βc tails of adjacent hexamers are ~10 Å apart thus providing a molecular explanation of how GM-CSF binding can initiate receptor transphosphorylation through pairs of βc tails. Furthermore, in the dodecamer complex the GM-CSFRα cytoplasmic tails are ~30 Å from the βc cytoplasmic tails of each neighboring hexamer (FIG. 4). Thus the dodecamer structure also explains how the cytoplasmic domains from both subunits could participate in signaling (FIG. 4C).

Although preformed GM-CSFRα-βc complexes can occur on the surface of un-stimulated cells (Woodcock et al, supra 1997) suggesting that βc and GM-CSFRα have intrinsic affinity, the assembly of functionally active complexes normally requires GM-CSF. The existence of cytokine-independent βc mutants that are only able to signal in an alpha subunit-dependent manner is consistent with an essential role for the alpha subunit in βc signaling complexes. Duplication of βc residues 395 to 431 or deletions that remove all βc extracellular residues up to 395 yield cytokine-independent signaling (D'Andrea et al, supra 1996) as do a range of point mutations that target residues in domain 4 (Jenkins et al, supra 19967). These results suggest that following structural rearrangement or misfolding, residues 395-431 of βc are available to functionally interact with GM-CSFRα in a cytokine-independent manner. Interestingly, residues 395 to 400 of βc are located in the hexamer contact region with GM-CSFRα and supply the major surface for the Site 3 interaction between βc and GM-CSFRα (FIG. 2). Dodecamer formation offers a unifying mechanism for ligand-dependent and -independent activation of the GM-CSF receptor.

Figure 3:
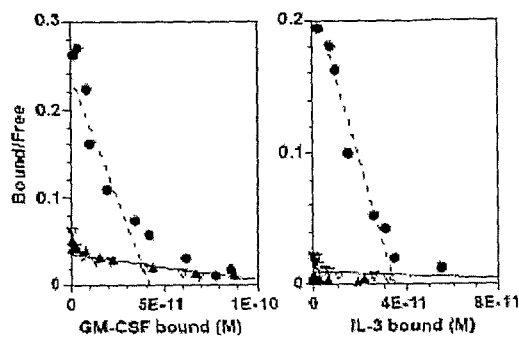
Figure 3:
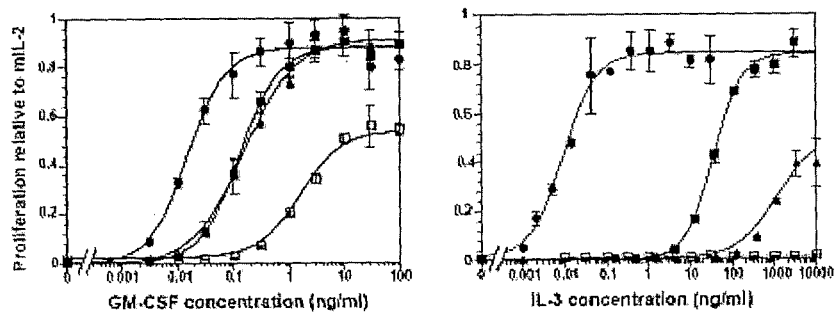

The βc-dependent cytokines GM-CSF, IL-3 and IL-5 exhibit less than 15% sequence identity to one another with most of the similarity located in the cores of each protein (Kaushansky and Karplus, *Blood* 82:3229, 1993). Mutagenesis of the conserved glutamate in helix A of these cytokines dramatically reduces functional interaction with βc (Site 2) but not alpha chain (Hercus et al, supra 1994; Barry et al, *J. Biol. Chem.* 269:8488, 1994; Tavernier et al, *Proc. Natl. Acad. Sci. USA* 92:5194, 1995). It is interesting to note that although there is a loss of high-affinity GM-CSF or IL-3 binding through combined mutagenesis of the cytokine binding contacts in βc domain 4, IL-3 but not GM-CSF signaling is abolished (FIG. 3B). Thus, while the structure shown here impacts on the receptor family as a whole, the results are consistent with subtle differences in βc recognition by each cytokine. IL-5 is unique amongst cytokines utilizing βc in that it forms a disulfide-linked dimer. This dimer is modeled into the dodecamer complex (FIG. 8) and it is concluded that one monomer of IL-5 could engage one βc dimer from each hexameric complex without compromising dodecamer formation.

Sequence alignments show the interfaces between the various chains are well conserved between the GM-CSF, IL-3 and IL-5 receptors suggesting the insights derived here for the GM-CSF receptor are likely to apply, with varying degrees, to the other two receptors. Thus, dodecamer assembly likely represents a common mechanism of signaling by GM-CSF, IL-3 and IL-5 and offers novel opportunities to modulate their functions.

Example 3

Total Protein Concentration and Stoichiometry of the GM-CSF Ternary Complex

Figure 6:
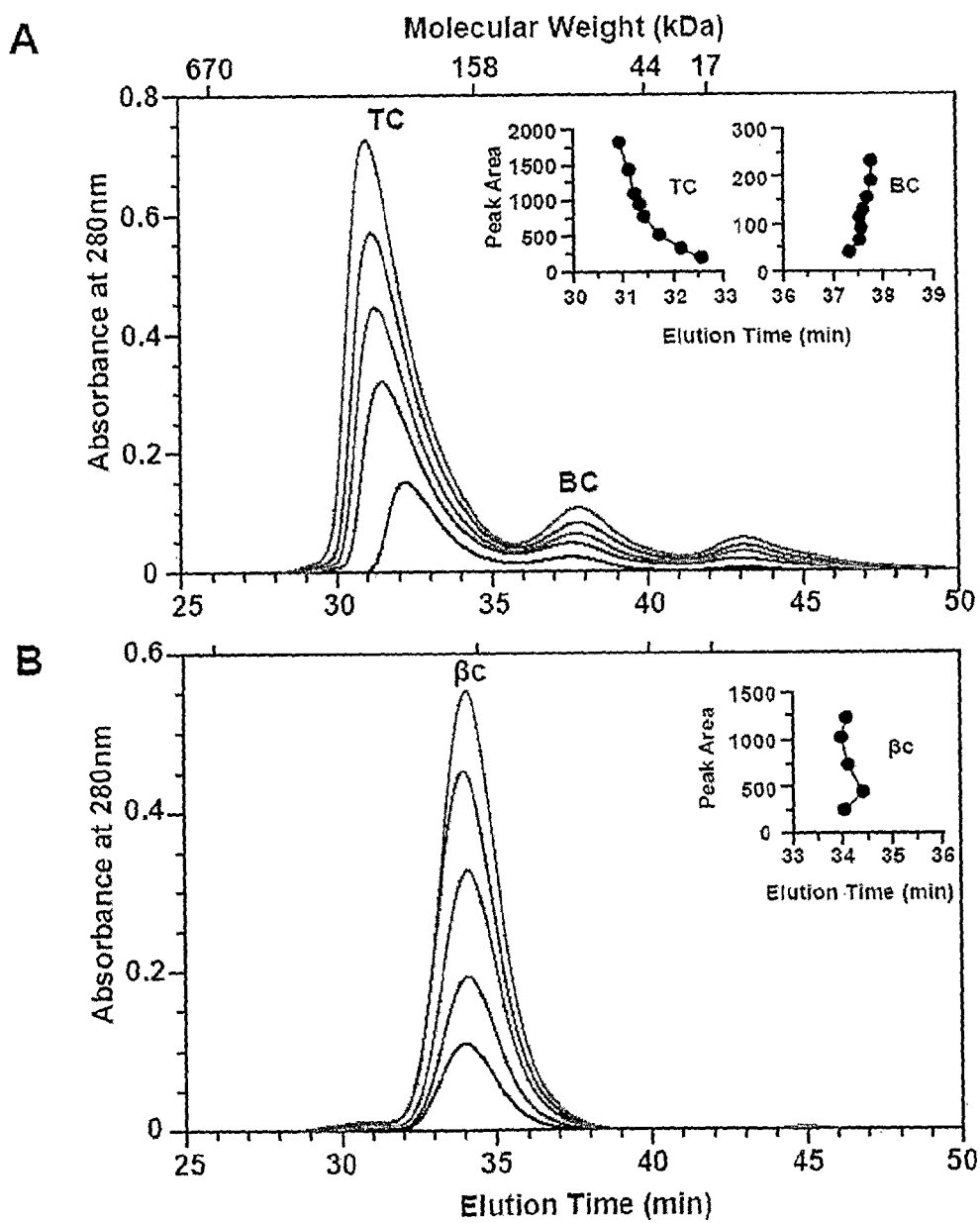

Formation and stoichiometry of the soluble ternary complex were characterized by a number of different techniques, usually at protein concentrations in the low micromolar range (McClure et al, supra 2003). For preparation of material used in crystallization studies, considerably higher protein concentrations (~30 μM) are used. The fact that the stoichiometry of the crystallized ternary complex differs from what was observed in previous studies prompted an investigation into the impact of protein concentration on the stoichiometry of the GM-CSF ternary complex. Purified sβc (1.1-10.7 μM) was titrated alone or in the presence of equimolar sGM-CSFRα and a 1.5× molar excess of GM-CSF and fractionated the mixture by size exclusion chromatography (FIG. 6). The elution time of the ternary complex (TC) was markedly influenced by total protein concentration unlike the GM-CSFRα: GM-CSF binary complex (BC) or free sβc. At the lowest sβc concentration (1.1 μM), the resulting ternary complex elutes at 32.6 minutes whilst at the highest sβc concentration (10.7 μM), the ternary complex elutes at 30.9 minutes. The differences in elution time suggest an increase in molecular weight of the ternary complex at higher protein concentrations that is consistent with a possible change in stoichiometry from 2 sβc: 1 sGM-CSFRα: 1 GM-CSF at low protein concentrations to 2 sβc: 2 sGM-CSFRα: 2 GM-CSF at high protein concentrations. This would explain the differences in stoichiometry observed for the ternary complex and may indicate that there are relatively stable intermediates in the assembly of higher order GM-CSF receptor complexes.

Example 4

Modeling of the N-Terminal Knob Domain of GM-CSFRα

IL-3, IL-5 and GM-CSF receptors have been shown to undergo covalent dimerization of their respective α chains with βc in the presence of their cognate ligand and this appears to be essential for receptor activation (Stomski et al, *Mol. Cell. Biol.* 16:3035-3046, 1996; Stomski et al, *J. Biol. Chem.* 273:1192-1199, 1998). Modeling studies suggested the disulfide forms between domain 1 of βc and the knob domain of the α chain. It is not possible to homology model the knob region into the crystal structure of the hexamer complex so that it gets sufficiently close to domain 1 of the βc chain. However, the knob domain can be fit snugly between domain 1 of GM-CSFR α and domain 1 of βc from the second hexamer molecule in the dodecamer structure (FIG. 4A) providing further credence for the possible physiological relevance of the latter structure. This suggests a role for the knob in stabilizing the higher order signaling complexes for receptor signaling.

Example 5

Cytokine Recognition by Shared Receptors Analogies to the IL-2 and IL-6 Receptors Structurally the βc and α chains of the GM-CSF, IL-3 and IL-5 receptors belong to the family of cytokine class I receptors that includes receptors for growth hormone (GH), erythropoietin, IL-2, IL-4 and IL-6. The mechanism by which GM-CSF binds its receptor components exhibits some analogies to the model first developed for the GH signaling complex, the paradigm for hematopoietic signaling (Wells and de Vos, supra 1996) but is more analogous to heteromeric class 1 receptor systems (FIG. 7). For example, the IL-6/IL-6 receptor high-affinity hexameric complex also comprises two IL-6 molecules, two alpha chains (IL-6Rα) and two molecules of the shared gp130 signal transducing receptor. Cytokine binding occurs at the elbows made between contiguous domains of IL-6Rα and gp130 (FIG. 7B) (Boulanger et al, supra 2003). Like the GM-CSF receptor system, a low affinity complex first forms between site 1 of the IL-6 cytokine and its non-signaling alpha chain followed by generation of the high affinity signaling complex through cytokine site 2 binding with gp130.

The IL-2/IL-2 receptor quaternary complex comprises IL-2, an alpha chain (IL-2Rα), a beta chain (IL-2Rβ) and common gamma chain (γc). The crystal structure of the quaternary complex (Wang et al, supra 2005; Stauber et al, supra 2006) revealed that IL-2 binds to the elbow regions of IL-2Rα and γc (FIG. 7C) such that these chains are structurally analogous to GM-CSFRα and βc. However, unlike the first two, the GM-CSF shared receptor uses non-contiguous FnIII domains to recognize its cytokine. The interaction surfaces between the chains in the IL-2 and GM-CSF receptor systems are also similar: burying ~1500 Å$^2$ of surface area in the membrane proximal domains consisting of a hydrophobic core surrounded by a polar rim of interactions. It has been argued that the role of IL-2 is to stabilize the IL-2Rβ-γc complex by optimizing alignment of the numerous interactions in the membrane-proximal interface of the two chains. The capacity of the γc chain to recognize numerous cytokines but discriminate against many others is more readily achieved by spreading the energetics of interaction over the large surface area contributed by the IL-2/IL-2Rβ composite surface (Wang et al, supra 2005). Similar arguments could be put forward for the role of GM-CSF in its high affinity hexameric complex. However, it is proposed here that GM-CSF may play an additional role in stabilizing high order signaling complexes. The IL-2 and GM-CSF receptor systems appear to use a similar code in recognizing their common binding chains. In the IL-2 system $Gln^{126}$ has been suggested as a common contact point whereas in the GM-CSF system $Glu^{21}$ appears to play a similar role. Remarkably, in both systems there are no obvious clusters of conserved residues around either residue suggesting many different solutions are used for common chain recognition. The relatively flat and apparently rigid cytokine recognition surfaces seen in the shared receptors systems involving and gp130 chains is also observed in the βc chain of the GM-CSF complex, demonstrating how shared receptors bypass the entropic penalty that would be caused by conformational changes (Wang et al, supra 2005).

A feature of the IL-2 receptor is its use of a two domain-swapped "sushi" module in IL-2Rα to interact with a third site on IL-2. In the IL-6 system an N-terminal non-CRM domain (IGD) is also used to bind cytokine at a third site. By analogy, the N-terminal non-CRM, knob domain of GM-CSFRα may also contact cytokine and this possibility is supported by the observation that mutations in the knob domain of IL-3Rα (Barry et al, supra 1997) and IL-5Rα (Ishino et al, *J. Biol. Chem.* 279:9547, 2003) reduce cytokine binding.

Example 6

Docking of IL-5 Dimer onto Dodecameric Complex Model

Figure 8:
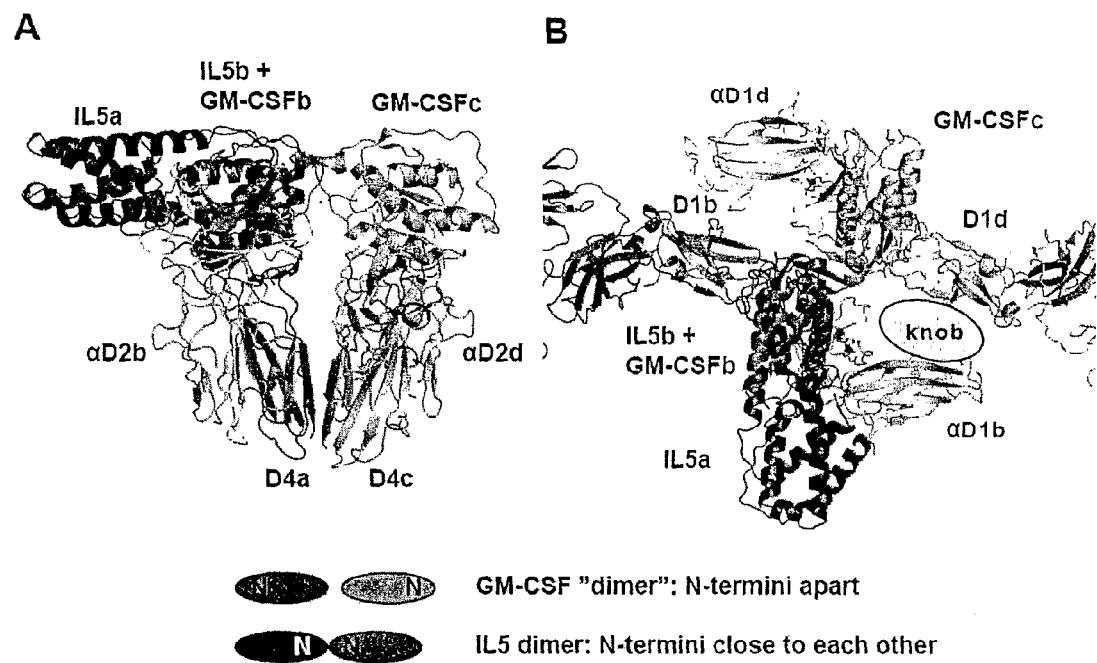

IL-5 forms a disulfide-linked dimer in which helix D of one chain combines with helices A, B and C of the other chain so that each four helix bundle of the dimer resembles the bundle observed in the monomeric GM-CSF and IL-3 molecules (FIG. 8). The possibility that IL-5 exerts its biological activity through both monomers has been supported by the observation that engineered dimers of mouse IL-3 display increased biological activity. The issue arises whether IL-5 dimer can dock onto the dodecamer complex where the GM-CSF "dimers" bind". The IL-5 dimer was superimposed onto GM-CSF in the dodecamer complex structure (FIG. 8). Because GM-CSF packs as a head-to-tail dimer in the complex whereas the IL-5 dimer assembles as a head-to-head dimer (with respect to the N-termini), the superposition results in one IL-5 monomer pointing out into solution. Attempts were made to dock the IL-5 dimer into the dodecamer complex so that both monomers interacted with βc molecules, assuming that at least one of the essential $Glu^{13}$ residues interacts with domain 4 of βc in similar fashion to how GM-CSF interacts with the same region. No convincing docking solution in which the IL-5 dimer interacting with both βc chains of the dodecamer could be identified. An IL-5 monomer was then superimposed onto GM-CSF in the hexameric complex and a dodecamer complex generated using the twofold axis observed in the IL-5 dimer, but the distance between equivalent βc cytoplasmic tails would be approximately 100 Å, too far apart for signaling to occur. Thus the IL-5 dimer likely functions as a monomer in the receptor complex. This suggestion is in agreement with the findings that the IL-5 dimer binds its alpha chain in a 1:1 ratio (Devos et al, *J. Biol. Chem.* 268:6581, 1993) and that engineered IL-5 monomers stimulate cell proliferation in IL-5 receptor positive cells with a dose dependence similar to wild-type (Li et al, *Proc. Natl. Acad. Sci. USA* 94:6694, 1997).

Example 7

Figure 9:
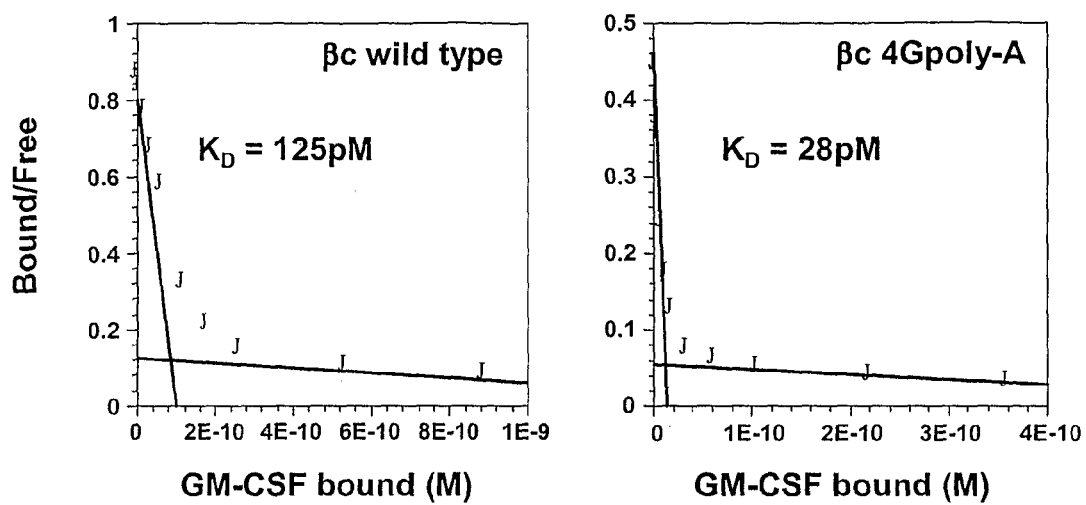
Figure 10:
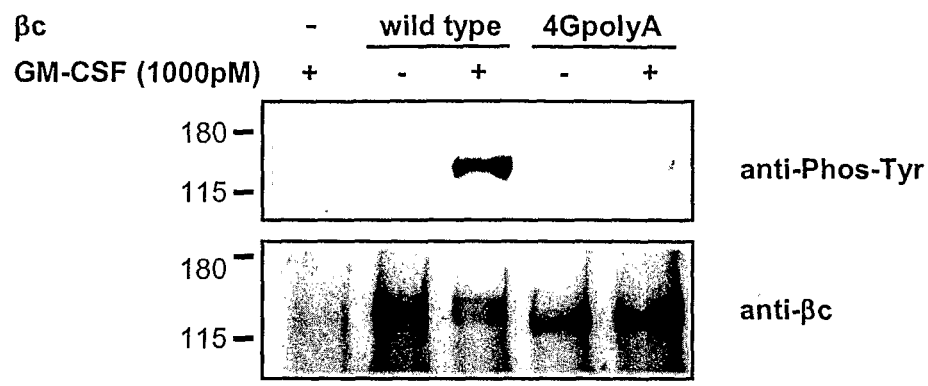
FIG. 10 is a photographic representation showing that GM-CSF induces tyrosine phosphorylation of wild type βc but not of the βc4 Gpoly-A (M7-βc) mutant in transfected CTL-EN/GMRα/IL3Rα cells.
Figure 11:
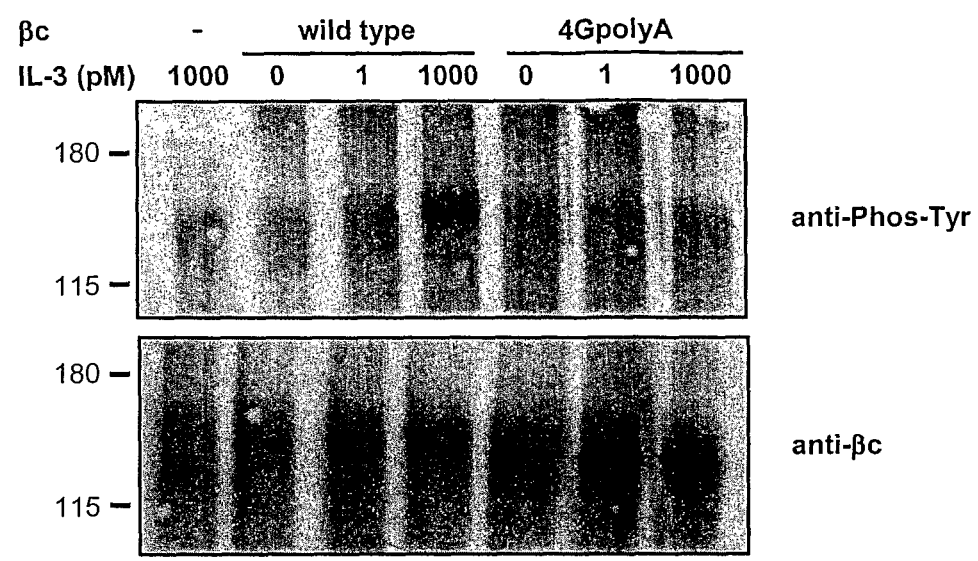
FIG. 11 is a photographic representation showing that IL-3 induces tyrosine phosphorylation of wild type βc but not of the βc4 Gpoly-A (M7-βc) mutant in transfected CTL-EN/GMRα/IL3Rα cells.

Mutation of βc at the Dodecamer Interface Abolishes GM-CSF and IL-3 Mediated, βc Tyrosine Phosphorylation but not GM-CSF High-Affinity Binding The crystal structure of the GM-CSF receptor complex reveals a dodecameric assembly. To determine if the formation of the dodecamer structure is required for function of the GM-CSF receptor, poly-alanine substitution of residues 430-435 in strand G of βc domain 4 (βc4 Gpoly-A) was used to disrupt Site 4 of the dodecamer interface. The βc4 Gpoly-A mutation (M7-βc) was designed where $^{430}$EARSWD$^{435}$ (SEQ ID NO:1) is replaced with $^{430}$AAAAAA$^{435}$ (SEQ ID NO:2). When transiently co-expressed with GMRα on COS cells, the βc4 Gpoly-A mutant generates high affinity binding sites for GM-CSF (FIG. 9) indicating that Sites 1, 2 and 3 of the receptor complex are not affected. The βc4 Gpoly-A mutant was transiently expressed in CTL-EN cells stably expressing GMRα and IL3Rα. Following stimulation with GM-CSF (1000 pM), wild type βc but not βc4 Gpoly-A was tyrosine phosphorylated (FIG. 10). Similarly, stimulation with 1000 μM IL-3 led to tyrosine phosphorylation of wild type βc but not βc4 Gpoly-A (FIG. 11). A lower dose of IL-3 (1 pM) did not allow tyrosine phosphorylation of wild type βc. The data indicate that βc interactions through the Site 4 contacts identified in the dodecamer complex are required for GM-CSF and IL-3 signaling but not for high-affinity ligand binding.

Example 8

Figure 12:
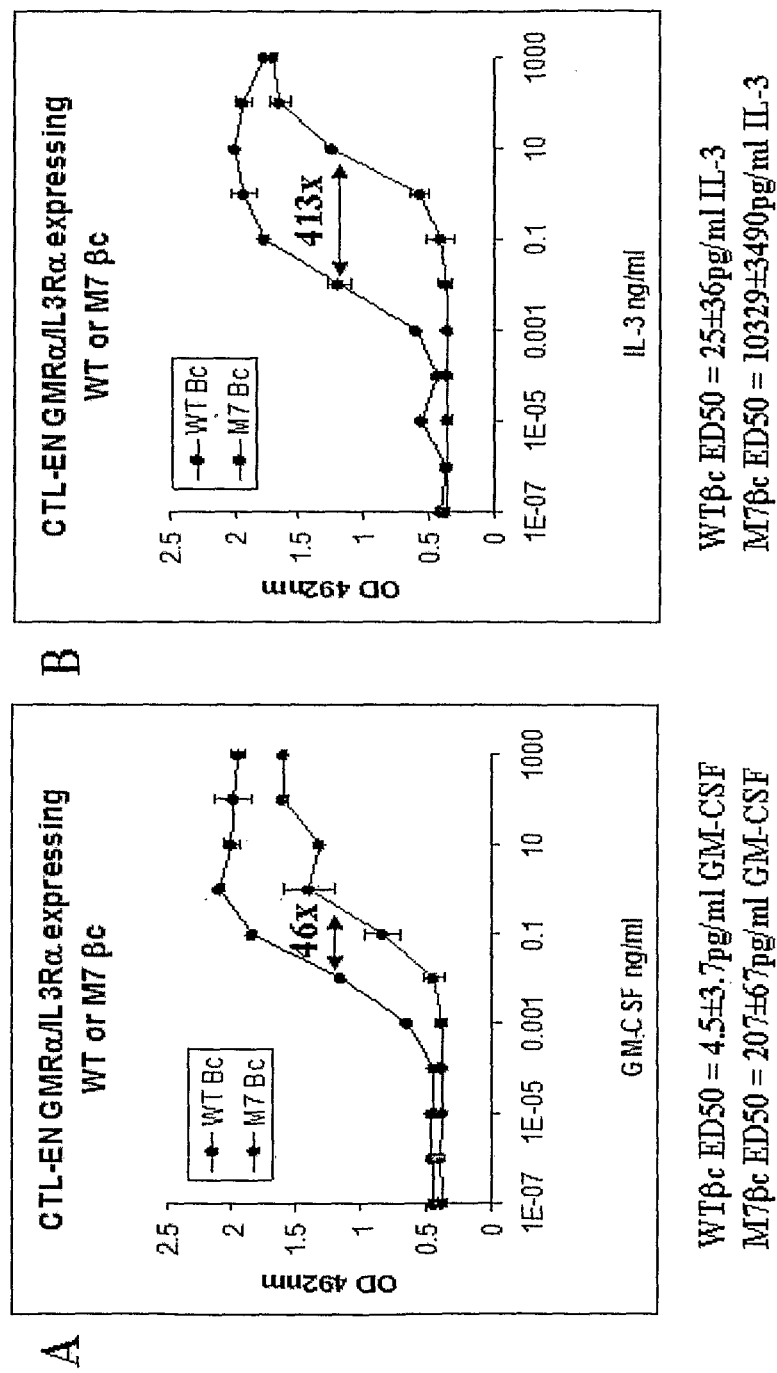
Figure 13:
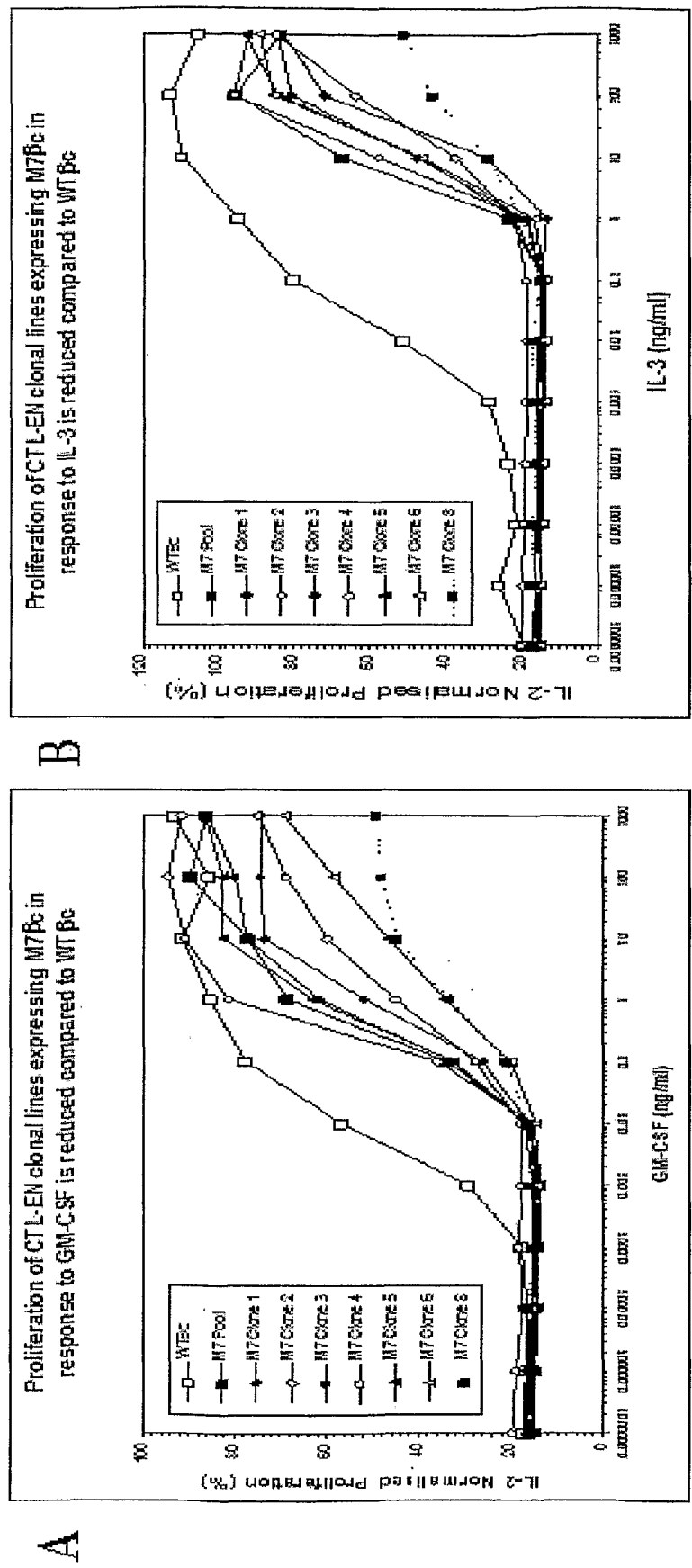

Mutation of βc at the Dodecamer Interface Abolishes GM-CSF and IL-3 Mediated Cell Proliferation and Tyrosine Phosphorylation of βc and Downstream Signalling Molecules To determine if the formation of the dodecamer structure is required for function of the GM-CSF receptor, both WTβc and M7βc were cloned into the pRcCMVpuro construct which was used to transfect the mIL2 dependent T-cell line CTL-EN expressing GMRα and IL3Rα. These lines CTL-EN GM-CSFRα/IL3Rα WTβc and CTL-EN GM-CSFRα/IL3Rα M7βc were assessed for their ability to proliferate in response to GM-CSF and IL-3 (FIG. 12). The presence of the M7 mutation in βc resulted in a reduced capacity to proliferate in response to GM-CSF (FIG. 12A) and IL-3 (FIG. 12B). In response to GM-CSF, the $ED_{50}$ was increased from 4.5±3.7 pg/ml to 207±67 pg/ml, approximately 46 fold (FIG. 12A). While in response to IL-3 the $ED_{50}$ was increased from 25±36 pg/ml to 10329±3490 pg/ml, approximately 413 fold (FIG. 12B). This was confirmed by the isolation of seven independent clonal lines expressing M7βc (FIG. 13). Each of these lines also show the same reduction in proliferative capacity to GM-CSF (FIG. 13A) and IL-3 (FIG. 13B), however each clone has a different maximal proliferation. The maximal proliferation correlates with the level of M7βc expression in the clones (FIG. 14). Interestingly, the reduction in GM-CSF and IL-3 proliferative response when signalling through the M7βc occurs despite its ability to confer high affinity GM-CSF binding akin to the WT GM-CSFR.

The biochemical results show that a βc receptor mutated at Site 4 has a deficient capacity to be tyrosine phosphorylated in response to either GM-CSF (FIG. 15A) or IL-3 (FIG. 15B). This is likely to be responsible for the defective proliferation seen above (FIGS. 12 and 13) as tyrosine phosphorylation of these receptors is well known to be needed for the transmission of a proliferative signal (Guthridge et al, *EMBO J.* 25:479-489, 2006). Not only the receptors are deficiently tyrosine phosphorylated but also two key signaling proteins, JAK-2 and STAT-5. The deficient phosphorylation of JAK-2 is particularly important because it supports the concept that Site 4 is necessary to bring two molecules of βc-associated JAK-2 molecules in close proximity for transphosphorylation and receptor activation to occur. This defective JAK-2 phosphorylation is, in turn, likely to be responsible for the poor STAT-5 phosphorylation seen in response to stimulation by either GM-CSF or IL-3 (FIGS. 15A and B). Both JAK-2 and STAT-5 have been clearly shown to be involved in proliferative signals by these receptors hence explaining the greatly reduced cell proliferation.

The corollary of these findings is that agents such as monoclonal antibodies or small molecules that interfere with Site 4 will reduce the phosphorylation of JAK-2, beta c and STAT-5 and consequently cell proliferation. Drugs that do this will be useful in the treatment of certain leukemias where GM-CSF and IL-3 induce their growth and in inflammation where these receptors stimulate the production of myeloid cells, dendritic cells and the effector cell function by myeloid cells Example 9

Testing of Anti-βc Site 4 Mab in a Monkey Model of Asthma

Antibodies are tested for preclinical safety, toxicity and tolerability in at least two animal species of which one is cynomolgus monkeys (*Macaca fascicularis*). Efficacy testing in a cynomolgus monkey model of asthma is undertaken based on general availability and the fact that these models offer advantages over asthma models performed in other species most especially an increased relevance for human disease (Coffman & Hessel, *J. Exp. Med.* 201:1875-1879, 2005).

Studies using an *Ascaris suum* airway challenge model of allergic asthma are performed essentially as described by Bree et al, *J. Allergy Clin. Immunol.* 119:1251-1257, 2007 and similar methodology is also described for example in Wegner et al, *Science* 247:456-459, 1990; Gundel et al, *J. Clin. Invest.* 88:1407-1411, 1991; Mauser et al, *Am. J. Respir. Crit. Care Med.* 152:467-472, 1995; Egan et al, *Mem Inst Oswaldo Cruz, Rio de Janeiro* 92 Suppl. 69-73, 1997; Hart et al, *J. Allergy Clin. Immunol.* 108:250-257, 2001.

Test antibodies are formulated in saline, 20 mM L-histidine, pH6.2 and is administered by intravenous infusion. Test animals are selected based on sensitivity and known airway hyperresponsiveness to *A. suum*. Each animal's untreated response to antigen is evaluated 6 weeks before antibody administration to establish a baseline response.

Treatment groups each containing 8 animals, include vehicle control and test antibody administered at each of 0.1, 1, 10 and 100 mg/kg. Twenty four hours after test antibody treatment animals are anaesthetised, intubated, maintained on a ventilator and *A. suum* antigen administered by aerosol to induce a bronchoconstrictor response. Lung function is assessed during the session by measuring lung resistance and decreases in dynamic compliance. Bronchoalveolar lavage (BAL) fluid is collected by instilling 20 mL aliquots of warm sterile saline into the lung, fluid removed and collected for cellular analysis of lung inflammation and cytokine levels.

In addition, 24 hours later, airway hyperresponsiveness (AHR) is measured by administration of varying doses of histamine to the animals and the dose required to cause hyperactivity is compared to the dose established prior to treatment (Egan et al, supra 1997).

Blood samples are taken at intervals commencing immediately before antibody treatment (day 0), day 1, day 2, day 3, week 1, week 4 and week 8 after *A. suum* challenge and are used to assess clinical haemotology and measure IgE and circulating test antibody levels.

Therapeutic effect of test antibody relative to control group is assessed as attenuation of airway hyperactivity and improvement in lung function following *A. suum* and histamine challenge. Efficacy is assessed as decreased infiltration of inflammatory cells into the lung including eosinophils, mast cells, macrophages, TH2 lymphocytes and neutrophils. Evidence of therapeutic effect is also assessed as decreased levels of inflammatory mediators including the cytokines IL-4, IL-5, IL-13, TNFα, IL-6, GM-CSF and IL-3, the chemokines eotaxin, RANTES, MCP-1, MIP-1, IL-8 and the inflammatory mediators prostaglandin E2, leukotriene B4, histamine and platelet activating factor. Decreased serum total IgE and *A. suum*-specific IgE levels are also markers of therapeutic effect.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

*Acta Crystallogr. D Biol. Crystallogr.* 50:760, 1994
Barry et al, *J. Biol. Chem.* 269:8488, 1994
Bird et al, *Science* 242:423-426, 1988
Boulanger et al, *Science* 300:2101, 2003
Bree et al, *Allergy Clin. Immunol.* 119:1251-1257, 2007
Carr et al, *Cell* 104:291, 2001
Carr et al, *Acta Crystallogr. F* 62:509, 2006
Chen et al, *International Immunology* 5:647-656, 1993
Chen et al, *EMBO J.* 12:821-830, 1993
Choi et al, *Nature Genetics* 4:117-123, 1993
Chothia et al, *J. Mol. Biol.* 196:901, 1987
Chou et al, U.S. Pat. No. 6,056,957
Coligan et al, *Current Protocols in Immunology,* 1991-1997
Coffman & Hessel, *J. Exp. Med.* 201:1875-1879, 2005
Cook et al, *Proc. Natl. Acad. Sci. USA* 94:6694, 1997
D'Andrea et al, *Blood* 87:2641, 1996
DeLano, The PyMOL Molecular Graphics System, DeLano Scientific, San Carlos, Calif. USA, 2002
Devos et al, *J. Biol. Chem.* 268:6581, 1993
EP 0 154 316
EP 0 401 384
EP 1 176 195
EP 0 239 400
Egan et al, *Mem Inst Oswaldo Cruz, Rio de Janeiro* 92 *Suppl. II:* 69-73, 1997
Fishwild et al, *Nature Biotechnology* 14:845-851, 1996
Fleetwood et al, *Crit. Rev. Immunol.* 25:405, 2005
Gefter et al, *Samatic Cell Genet.* 3:231-236, 1977

Goding, *Monoclonal Antibodies: Principles and Practice 2nd Ed.*, New York: Academic, 1986
Gundel et al, *J. Clin. Invest.* 88:1407-1411, 1991
Guthridge et al, *Stem Cells* 16:301, 1998
Guthridge et al, *EMBO J* 25:479-489, 2006
Harding and Lonberg, *Ann. N.Y. Acad. Sci.* 764:536-546, 1995
Hart et al, *J. Allergy Clin. Immunol.* 108:250-257, 2001
Heckman and Pease, *Nature Protocols* 2:924-932, 2007
Hercus et al, *Proc. Natl. Acad. Sci. USA* 91:5838, 1994
Hercus et al, *Blood* 83:3500, 1994
Holt et al, *Trends in Biotechnology*, 21:484-489, 2003
Huston et al, *Proc. Natl. Acad. Sci. USA* 85:5879-5883, 1988
Ishino et al, *J. Biol. Chem.* 279:9547, 2003
Jenkins et al, *J. Biol. Chem.* 271:29707, 1996
Jenkins and Gonda, *J. Biol. Chem.* 274:8669, 1999
Jones et al, *Nature* 321:522-525, 1986
Kabat et al, *Sequences of Proteins of Immunological Interest, Fifth Edition*, U.S. Department of Health and Human Services, NIH Publication No. 91:3242, 1991
Kaushansky and Karplus, *Blood* 82:3229, 1993
Kitamura et al, *J. Cell Physiol.* 140:323-34, 1989
Kohler et al, *Nature* 256:495-499, 1975
Kholer et al, *Eur. J. Immunol.* 6(7):511-519, 1976
Kozbar et al, *Methods in Enzymology* 121:140, 1986
Li et al, *Proc. Natl. Acad. Sci. USA* 94:6694, 1997
Lia et al, *J. Biol. Chem.* 271:28287, 1996
Lieu et al, *Proc. Natl. Acad. Sci. USA* 84:3439-3443, 1987
Lock et al, *Proc. Natl. Acad. Sci. USA* 91:252, 1994
Lonberg, et al, *Nature* 368(6474):856-859, 1994
Lonberg, *Handbook of Experimental Pharmacology* 113:49-101, 1994; Lonberg and
Huszar, *Intern. Rev. Immunol.* 13:65-93, 1995
McClure et al, *Blood* 101:1308, 2003
Mark et al, *Handbook of Experimental Pharmacology vol. 113: The pharmacology of monoclonal Antibodies*, Springer-Verlag, pp 105-134, 1994
Mauser et al, *Am. Respir. Crit. Care Med.* 152:467-472, 1995
Morgan et al, U.S. Pat. No. 6,180,377
Munson and Rodbard, *Anal. Biochem.* 107:220, 1980
Murphy et al, *J. Biol. Chem.* 278:10572, 2003
Murphy et al, *J. Biol. Chem.* 279:26500, 2004
Murshudov et al, *Acta Crystallogr. D* 53:240, 1997
Muto et al, *Biochem. Biophys. Res. Commun.* 208:368, 1995
Noren et al, *Science* 244:182-188, 1989
Padlan et al, *Mol. Immunol.* 28:489-498, 1991
Painter and Merritt, *Acta Crystallogr. D* 62:439, 2006
Pedersen et al, *J. Mol. Biol.* 235:959-973, 1994
Queen et al, U.S. Pat. No. 6,180,377
Rajotte et al, *J. Exp. Med.* 185:1939, 1997
Richmann et al, *Nature* 332:323-327, 1988
Rossjohn et al, *Blood* 95:2491, 2000
Rozwarski et al, *Proteins* 26:304, 1996
Shields et al, *J. Biol. Chem.* 277:26733-26740, 2002
Stauber et al, *Proc. Natl. Acad. Sci. USA* 103:2788, 2006
Stomski et al, *Mol. Cell. Biol.* 16:3035-3046, 1996
Stomski et al, *J. Biol. Chem.* 273:1192-1199, 1998
Storoni et al, *Acta Crystallogr. D* 60:432, 2004
Sun et al, *Blood*, 94:1943-1951, 1999
*Sustained and Controlled Release Drug Delivery Systems*, Robinson, ed., Marcel Dekker, Inc., New York, 1978
Tavernier et al, *Proc. Natl. Acad. Sci. USA* 92:5194, 1995
Taylor et al, *Nucleic Acids Research* 20:6287-6295, 1992
Taylor et al, *International Immunology* 6:579-591, 1994
Tuaillon et al, *Proc. Natl. Acad. Sci. USA* 90:3720-3724, 1993
Tuaillon et al, *J. Immunol.* 152:2912-2920, 1994
Toyama et al, *Monoclonal Antibody, Experimental Manual*, published by Kodansha Scientific, 1987
Umana et al, *Nat. Biotech.* 17:176-180, 1999
U.S. Patent No. 20030153043
U.S. Pat. No. 4,790,824
U.S. Pat. No. 4,816,567
U.S. Pat. No. 5,064,413
U.S. Pat. No. 5,403,484
U.S. Pat. No. 5,223,409
U.S. Pat. No. 5,225,539
U.S. Pat. No. 5,312,335
U.S. Pat. No. 5,383,851
U.S. Pat. Nos. 5,399,163
U.S. Pat. No. 5,427,908
U.S. Pat. No. 4,596,556
U.S. Pat. No. 4,941,880
U.S. Pat. No. 5,530,101
U.S. Pat. No. 5,545,806
U.S. Pat. No. 5,545,807
U.S. Pat. No. 5,571,698
U.S. Pat. No. 5,569,825
U.S. Pat. No. 5,585,089
U.S. Pat. No. 5,580,717
U.S. Pat. No. 5,624,821
U.S. Pat. No. 5,625,126
U.S. Pat. No. 5,633,425
U.S. Pat. No. 5,648,260
U.S. Pat. No. 5,661,016
U.S. Pat. No. 5,677,425
U.S. Pat. No. 5,693,762
U.S. Pat. No. 5,714,350
U.S. Pat. No. 5,770,429
U.S. Pat. No. 5,789,650
U.S. Pat. No. 5,814,318
U.S. Pat. No. 5,869,046
U.S. Pat. No. 5,874,299
U.S. Pat. No. 5,877,397
U.S. Pat. No. 5,885,793
U.S. Pat. No. 5,969,108
U.S. Pat. No. 6,121,022
U.S. Pat. No. 6,165,745
U.S. Pat. No. 6,121,022
U.S. Pat. No. 6,172,197
U.S. Pat. No. 6,180,370
U.S. Pat. No. 6,350,861
U.S. Pat. No. 6,521,404
U.S. Pat. No. 6,544,731
U.S. Pat. No. 6,555,313
U.S. Pat. No. 6,582,915
U.S. Pat. No. 6,593,081
Verhoeyen et al, *Science* 239:1534-1536, 1988
Volk et al, *J Virol* 42(1):220-227, 1982
Wang et al, *Science* 310:1159, 2005
Ward et al, *Nature* 341:544-546, 1989
Wegner et al, *Science* 247:456-459, 1990
Wells and de Vos, *Annu. Rev. Biochem.* 65:609, 1996
Winn et al, *Acta Crystallogr. D* 57:122, 2001
WO 92/03918
WO 93/02108
WO 93/12227
WO 94/25585
WO 97/13852
WO 98/24884
WO 99/45962
WO 99/54342
WO 99/55369
WO 01/14424

WO 02/43478
WO 03/035835
WO 2004/006955

Woodcock et al, *EMBO J.* 13:5176, 1994
Woodcock et al, *J. Biol. Chem.* 271:25999, 1996
Woodcock et al, *Blood* 90:3005, 1997

LENGTHY TABLES

The patent contains a lengthy table section. A copy of the table is available in electronic form from the USPTO web site (http://seqdata.uspto.gov/?pageRequest=docDetail&DocID=US08489339B2). An electronic copy of the table will also be available from the USPTO upon request and payment of the fee set forth in 37 CFR 1.19(b)(3).

The invention claimed is:

1. A method of drug selection comprising,
   a) obtaining a crystal belonging to the space group P6₃22 with unit cell dimensions a=b=166.6 Å and c=213.1 Å, the crystal consisting of the polypeptide complex of GM-CSF of SEQ ID NO:16, soluble GM-CSFRα of SEQ ID NO:17 and soluble βc N346Q of SEQ ID NO:18;
   b) determining the three-dimensional structure of the complex by the X-ray diffraction method to obtain the atomic coordinates in Table 1;
   c) screening the atomic coordinates of Table 1 against a database of chemical entities to identify a chemical entity putatively able to associate with an interactive surface between granulocyte macrophage-colony stimulating factor (GM-CSF), GM-CSF receptor subunit alpha (GM-CSFRα) and GM-CSF receptor subunit beta-c (βc), wherein the interactive surface is selected from the group consisting of:
      (i) a site on GM-CSF defined by amino acid residues 11 to 23 and 112 to 118 of SEQ ID No. 16,
      (ii) a site on GM-CSFRα selected from:
         (a) amino acid residues 241 to 251 and 299 to 305 of SEQ ID No. 17,
         (b) amino acid residues 231, 232, 259, 266 to 270 and 280 to 286 of SEQ ID No. 17, and
         (c) amino acid residues 260 and 261 of SEQ ID No. 17,
      (iii) a site on βc selected from:
         (a) amino acid residues 106 to 113, 360 to 369 and 417 to 423 of SEQ ID No. 18,
         (b) amino acid residues 346 to 354, 357, 359, 362 and 430 to 435 of SEQ ID No. 18, and
         (c) amino acid residues 350, 353, 366 to 369, 389 to 400, and 418 of SEQ ID No. 18,
   d) selecting a chemical entity which computationally associates with the interactive surface for testing in a GM-CSF activity assay,
   e) incorporating said selected chemical entity into a biological cytokine activity assay; and
   f) determining whether said chemical entity inhibits the biological activity of human GM-CSF-mediated signaling.

2. The method of claim 1 wherein said chemical entity is an antagonist of human GM-CSF-mediated signaling.

3. The method of claim 1 wherein said chemical entity is an antagonist of signaling mediated by human interleukin (IL)-3, IL-5, erythropoietin (EPO), thrombopoietin (TPO) or c-kit ligand.

4. The method according to claim 2 wherein said chemical entity further antagonizes signaling mediated by human interleukin (IL)-3, IL-5, erythropoietin (EPO), thrombopoietin (TPO) or c-kit ligand.

5. A process of identifying a modulator of granulocyte macrophage-colony stimulating factor (GM-CSF)/GM-CSF receptor interaction and signaling, wherein said process comprises:

a) obtaining a crystal belonging to the space group $P6_322$ with unit cell dimensions a=b=166.6 Å and c=213.1 Å, the crystal consisting of the polypeptide complex of GM-CSF of SEQ ID NO:16, soluble GM-CSFRα of SEQ ID NO:17 and soluble βc N346Q of SEQ ID NO:18;

b) determining the three-dimensional structure of the complex by the X-ray diffraction method to obtain the atomic coordinates in Table 1;

c) computationally designing said modulator for interactions with a site determined from the atomic coordinates of a human GM-CSF/GM-CSFR crystal as set forth in Table 1, wherein said site is selected from the group consisting of:
   (i) a site on GM-CSF defined by amino acid residues 11 to 23 and 112 to 118 of SEQ ID No. 16,
   (ii) a site on granulocyte macrophage-colony stimulating factor receptor subunit alpha (GM-CSFRα) selected from:
      (a) amino acid residues 241 to 251 and 299 to 305 of SEQ ID No. 17,
      (b) amino acid residues 231, 232, 259, 266 to 270 and 280 to 286 of SEQ ID No. 17, and
      (c) amino acid residues 260 and 261 of SEQ ID No. 17,
   (iii) a site on GM-CSF receptor subunit beta-c (βc) selected from
      (a) amino acid residues 106 to 113, 360 to 369 and 417 to 423 of SEQ ID No. 18,
      (b) amino acid residues 346 to 354, 357, 359, 362 and 430 to 435 of SEQ ID No. 18, and
      (c) amino acid residues 350, 353, 366 to 369, 389 to 400, and 418 of SEQ ID No. 18; and d) determining whether said modulator inhibits the biological activity of human GM-CSF-mediated signaling in a GM-CSF activity assay.

6. The method of claim 5, wherein said modulator further modulates signaling by interleukin (IL)-3, IL-5, erythropoietin (EPO), thrombopoietin (TPO) or c-kit ligand.

* * * * *

```
                           SEQUENCE LISTING

<160> NUMBER OF SEQ ID NOS: 18

<210> SEQ ID NO 1
<211> LENGTH: 6
<212> TYPE: PRT
<213> ORGANISM: Homo sapiens
<220> FEATURE:
<221> NAME/KEY: misc_feature
<223> OTHER INFORMATION: Amino acid sequence present at Site 4 of beta-c

<400> SEQUENCE: 1

Glu Ala Arg Ser Trp Asp
1               5

<210> SEQ ID NO 2
<211> LENGTH: 5
<212> TYPE: PRT
<213> ORGANISM: Homo sapiens
<220> FEATURE:
<221> NAME/KEY: misc_feature
<223> OTHER INFORMATION: amino acid sequence present in mutant M7 of
      Site 4 of beta-c

<400> SEQUENCE: 2

Ala Ala Ala Ala Ala
1               5

<210> SEQ ID NO 3
<211> LENGTH: 13
<212> TYPE: PRT
<213> ORGANISM: Homo sapiens
<220> FEATURE:
<221> NAME/KEY: misc_feature
<223> OTHER INFORMATION: Amino acid sequence present at Site 1 of GM-CSF

<400> SEQUENCE: 3

Thr Val Ala Cys Ser Ile Ser Ala Pro Ala Arg Ser Pro
1               5                   10

<210> SEQ ID NO 4
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence present at Site 1 of GM-CSF

<400> SEQUENCE: 4

Ser Cys Ala Thr Gln Ile Ile
1               5
```

-continued

```
<210> SEQ ID NO 5
<211> LENGTH: 11
<212> TYPE: PRT
<213> ORGANISM: Homo sapiens
<220> FEATURE:
<221> NAME/KEY: misc_feature
<223> OTHER INFORMATION: Amino acid sequence present at Site 1 of
      GM-CSFR alpha

<400> SEQUENCE: 5

Arg Thr Tyr Gln Lys Leu Ser Tyr Leu Asp Phe
1               5                   10

<210> SEQ ID NO 6
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence present at Site 1 of
      GM-CSFR alpha

<400> SEQUENCE: 6

Ala Asp Val Arg Ile Leu Asn
1               5

<210> SEQ ID NO 7
<211> LENGTH: 5
<212> TYPE: PRT
<213> ORGANISM: Homo sapiens
<220> FEATURE:
<221> NAME/KEY: misc_feature
<223> OTHER INFORMATION: Amino acid sequence present at Site 3 of
      GM-CSFR alpha

<400> SEQUENCE: 7

Thr Glu Asn Leu Leu
1               5

<210> SEQ ID NO 8
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence present at Site 1 of
      GM-CSFR alpha

<400> SEQUENCE: 8

Arg Tyr Asn Phe Pro Ser Ser
1               5

<210> SEQ ID NO 9
<211> LENGTH: 8
<212> TYPE: PRT
<213> ORGANISM: Homo sapiens
<220> FEATURE:
<221> NAME/KEY: misc_feature
<223> OTHER INFORMATION: Amino acid sequence present at Site 2 of beta-c

<400> SEQUENCE: 9

Thr Asp Val Asp Tyr Phe Ser Phe
1               5

<210> SEQ ID NO 10
<211> LENGTH: 10
<212> TYPE: PRT
<213> ORGANISM: Homo sapiens
<220> FEATURE:
<221> NAME/KEY: misc_feature
```

<223> OTHER INFORMATION: Amino acid sequence present at Site 2 of beta-c

<400> SEQUENCE: 10

Thr Met Lys Met Arg Tyr Glu His Ile Asp
1               5                   10

<210> SEQ ID NO 11
<211> LENGTH: 7
<212> TYPE: PRT
<213> ORGANISM: Homo sapiens
<220> FEATURE:
<221> NAME/KEY: misc_feature
<223> OTHER INFORMATION: Amino acid sequence present at Site 2of beta-c

<400> SEQUENCE: 11

Ser Arg Thr Gly Tyr Asn Gly
1               5

<210> SEQ ID NO 12
<211> LENGTH: 9
<212> TYPE: PRT
<213> ORGANISM: Homo sapiens
<220> FEATURE:
<221> NAME/KEY: misc_feature
<223> OTHER INFORMATION: Amino acid sequence present at Site 4 of beta-c

<400> SEQUENCE: 12

Asn Val Thr Lys Asp Gly Asp Ser Tyr
1               5

<210> SEQ ID NO 13
<211> LENGTH: 4
<212> TYPE: PRT
<213> ORGANISM: Homo sapiens
<220> FEATURE:
<221> NAME/KEY: misc_feature
<223> OTHER INFORMATION: Amino acid sequence present at Site 3 of beta-c

<400> SEQUENCE: 13

Glu His Ile Asp
1

<210> SEQ ID NO 14
<211> LENGTH: 12
<212> TYPE: PRT
<213> ORGANISM: Homo sapiens
<220> FEATURE:
<221> NAME/KEY: misc_feature
<223> OTHER INFORMATION: Amino acid sequence present at Site 3 of beta-c

<400> SEQUENCE: 14

Glu Thr Leu Gln Asn Ala His Ser Met Ala Leu Pro
1               5                   10

<210> SEQ ID NO 15
<211> LENGTH: 696
<212> TYPE: PRT
<213> ORGANISM: Homo sapiens
<220> FEATURE:
<221> NAME/KEY: MISC_FEATURE
<222> LOCATION: (413)..(413)
<223> OTHER INFORMATION: Xaa is Asparagine modified with a
      N-acetylglucosamine, N-acetylglucosamine, Mannose carbohydrate
      chain
<220> FEATURE:
<221> NAME/KEY: MISC_FEATURE
<222> LOCATION: (414)..(414)
<223> OTHER INFORMATION: Xaa is Asparagine modified with a
      N-acetylglucosamine residue

<400> SEQUENCE: 15

```
Glu Glu Thr Ile Pro Leu Gln Thr Leu Arg Cys Tyr Asn Asp Tyr Thr
  1               5                  10                  15
Ser His Ile Thr Cys Arg Trp Ala Asp Thr Gln Asp Ala Gln Arg Leu
             20                  25                  30
Val Asn Val Thr Leu Ile Arg Arg Val Asn Glu Asp Leu Leu Glu Pro
         35                  40                  45
Val Ser Cys Asp Leu Ser Asp Asp Met Pro Trp Ser Ala Cys Pro His
     50                  55                  60
Pro Arg Cys Val Pro Arg Arg Cys Val Ile Pro Cys Gln Ser Phe Val
 65                  70                  75                  80
Val Thr Asp Val Asp Tyr Phe Ser Phe Gln Pro Asp Arg Pro Leu Gly
                 85                  90                  95
Thr Arg Leu Thr Val Thr Leu Thr Gln His Val Gln Pro Pro Glu Pro
            100                 105                 110
Arg Asp Leu Gln Ile Ser Thr Asp Gln Asp His Phe Leu Leu Thr Trp
        115                 120                 125
Ser Val Ala Leu Gly Ser Pro Gln Ser His Trp Leu Ser Pro Gly Asp
    130                 135                 140
Leu Glu Phe Glu Val Val Tyr Lys Arg Leu Gln Asp Ser Trp Glu Asp
145                 150                 155                 160
Ala Ala Ile Leu Leu Ser Asn Thr Ser Gln Ala Thr Leu Gly Pro Glu
                165                 170                 175
His Leu Met Pro Ser Ser Thr Tyr Val Ala Arg Val Arg Thr Arg Leu
            180                 185                 190
Ala Pro Gly Ser Arg Leu Ser Gly Arg Pro Ser Lys Trp Ser Pro Glu
        195                 200                 205
Val Cys Trp Asp Ser Gln Pro Gly Asp Glu Ala Gln Pro Gln Asn Leu
    210                 215                 220
Glu Cys Phe Phe Asp Gly Ala Ala Val Leu Ser Cys Ser Trp Glu Val
225                 230                 235                 240
Arg Lys Glu Val Ala Ser Ser Val Ser Phe Gly Leu Phe Tyr Lys Pro
                245                 250                 255
Ser Pro Asp Ala Arg Glu Glu Glu Cys Ser Pro Val Leu Arg Glu Gly
            260                 265                 270
Leu Gly Ser Leu His Thr Arg His His Cys Gln Ile Pro Val Pro Asp
        275                 280                 285
Pro Ala Thr His Gly Gln Tyr Ile Val Ser Val Gln Pro Arg Arg Ala
    290                 295                 300
Glu Lys His Ile Lys Ser Ser Val Asn Ile Gln Met Ala Pro Pro Ser
305                 310                 315                 320
Leu Gln Val Thr Lys Asp Gly Asp Ser Tyr Ser Leu Arg Trp Glu Thr
                325                 330                 335
Met Lys Met Arg Tyr Glu His Ile Asp His Thr Phe Glu Ile Gln Tyr
            340                 345                 350
Arg Lys Asp Thr Ala Thr Trp Lys Asp Ser Lys Thr Glu Thr Leu Gln
        355                 360                 365
Asn Ala His Ser Met Ala Leu Pro Ala Leu Glu Pro Ser Thr Arg Tyr
    370                 375                 380
Trp Ala Arg Val Arg Val Arg Thr Ser Arg Thr Gly Tyr Asn Gly Ile
385                 390                 395                 400
Trp Ser Glu Trp Ser Glu Ala Arg Ser Trp Asp Thr Xaa Xaa Glu His
                405                 410                 415
```

Val Asn Ala Ile Gln Glu Ala Arg Arg Leu Leu Asn Leu Ser Arg Asp
            420                 425                 430

Ala Ala Glu Met Glu Thr Val Glu Val Ser Glu Met Phe Asp Leu Gln
            435                 440                 445

Glu Pro Thr Cys Leu Gln Thr Arg Leu Glu Tyr Lys Gln Gly Leu Arg
450                 455                 460

Gly Ser Thr Lys Leu Lys Gly Pro Thr Met Met Ala Ser His Tyr Lys
465                 470                 475                 480

Gln His Cys Pro Thr Pro Glu Thr Ser Ala Thr Gln Ile Ile Thr Glu
                485                 490                 495

Ser Phe Lys Glu Asn Leu Lys Asp Leu Leu Val Ile Ala Asn Pro Pro
            500                 505                 510

Ser Asn Val Thr Val Arg Cys Asn Thr Thr His Cys Leu Val Arg Trp
            515                 520                 525

Lys Gln Pro Arg Thr Tyr Lys Leu Ser Tyr Leu Asp Gln Tyr Gln Leu
            530                 535                 540

Asp His Arg Lys Asn Thr Gln Pro Gly Thr Asn Leu Leu Ile Asn Val
545                 550                 555                 560

Ser Asp Leu Glu Asn Arg Tyr Asn Phe Pro Ser Ser Pro Arg Ala Lys
                565                 570                 575

His Ser Val Lys Ile Arg Ala Ala Asp Val Arg Ile Leu Asn Trp Ser
            580                 585                 590

Ser Trp Ser Glu Ala Ile Glu Phe Gly Gly Arg Glu Gly Thr Ala Ala
            595                 600                 605

Gln Asn Phe Ser Cys Phe Ile Asn Ala Asp Met Asn Cys Thr Trp Ala
            610                 615                 620

Arg Gly Pro Ala Pro Arg Asp Val Gln Tyr Phe Leu Tyr Ile Arg Asn
625                 630                 635                 640

Ser Lys Arg Arg Arg Glu Ile Arg Cys Pro Tyr Tyr Ile Gln Asp Gly
                645                 650                 655

Thr His Val Gly Cys His Leu Asp Asn Gly Leu Thr Ser Arg Asn Tyr
            660                 665                 670

Phe Leu Val Asn Gly Thr Ser Arg Glu Ile Gly Ile Gln Phe Phe Asp
            675                 680                 685

Ser Leu Leu Asp Thr Lys Lys Ile
            690                 695

<210> SEQ ID NO 16
<211> LENGTH: 144
<212> TYPE: PRT
<213> ORGANISM: Homo sapiens
<220> FEATURE:
<221> NAME/KEY: MISC_FEATURE
<223> OTHER INFORMATION: Human GM-CSF

<400> SEQUENCE: 16

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

```
Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Lys Glu Asn Leu Lys
        115                 120                 125

Asp Phe Leu Leu Val Ile Pro Phe Asp Cys Trp Glu Pro Val Gln Glu
130                 135                 140

<210> SEQ ID NO 17
<211> LENGTH: 320
<212> TYPE: PRT
<213> ORGANISM: Homo sapiens
<220> FEATURE:
<221> NAME/KEY: MISC_FEATURE
<223> OTHER INFORMATION: Soluble Human GM-CSF Receptor Subunit Alpha

<400> SEQUENCE: 17

Met Leu Leu Leu Val Thr Ser Leu Leu Cys Glu Leu Pro His Pro
1               5                   10                  15

Ala Phe Leu Leu Ile Pro Glu Lys Ser Asp Leu Arg Thr Val Ala Pro
            20                  25                  30

Ala Ser Ser Leu Asn Val Arg Phe Asp Ser Arg Thr Met Asn Leu Ser
        35                  40                  45

Trp Asp Cys Gln Glu Asn Thr Thr Phe Ser Lys Cys Phe Leu Thr Asp
50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
        115                 120                 125

Tyr Asn Ala Asp Leu Met Asn Cys Thr Trp Ala Arg Gly Pro Thr Ala
130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
        195                 200                 205

Leu Leu Asp Thr Lys Lys Ile Glu Arg Phe Asn Pro Pro Ser Asn Val
210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
                245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
        275                 280                 285

Arg Ala Lys His Ser Val Lys Ile Arg Ala Ala Asp Val Arg Ile Leu
290                 295                 300
```

-continued

```
Asn Trp Ser Ser Trp Ser Glu Ala Ile Glu Phe Gly Ser Leu Gly Tyr
305                 310                 315                 320

<210> SEQ ID NO 18
<211> LENGTH: 438
<212> TYPE: PRT
<213> ORGANISM: Homo sapiens
<220> FEATURE:
<221> NAME/KEY: MISC_FEATURE
<223> OTHER INFORMATION: Human GM-CSF Receptor Subunit Beta-c
<220> FEATURE:
<221> NAME/KEY: MISC_FEATURE
<222> LOCATION: (346)..(346)
<223> OTHER INFORMATION: Substution of Q for N as compared to wild-type

<400> SEQUENCE: 18

Met Val Leu Ala Gln Gly Leu Leu Ser Met Ala Leu Leu Ala Leu Cys
1               5                   10                  15

Trp Glu Arg Ser Leu Ala Gly Ala Glu Glu Thr Ile Pro Leu Gln Thr
            20                  25                  30

Leu Arg Cys Tyr Asn Asp Tyr Thr Ser His Ile Thr Cys Arg Trp Ala
        35                  40                  45

Asp Thr Gln Asp Ala Gln Arg Leu Val Asn Val Thr Leu Ile Arg Arg
50                  55                  60

Val Asn Glu Asp Leu Leu Glu Pro Val Ser Cys Asp Leu Ser Asp Asp
65                  70                  75                  80

Met Pro Trp Ser Ala Cys Pro His Pro Arg Cys Val Pro Arg Arg Cys
                85                  90                  95

Val Ile Pro Cys Gln Ser Phe Val Val Thr Asp Val Asp Tyr Phe Ser
            100                 105                 110

Phe Gln Pro Asp Arg Pro Leu Gly Thr Arg Leu Thr Val Thr Leu Thr
        115                 120                 125

Gln His Val Gln Pro Pro Glu Pro Arg Asp Leu Gln Ile Ser Thr Asp
130                 135                 140

Gln Asp His Phe Leu Leu Thr Trp Ser Val Ala Leu Gly Ser Pro Gln
145                 150                 155                 160

Ser His Trp Leu Ser Pro Gly Asp Leu Glu Phe Glu Val Val Tyr Lys
                165                 170                 175

Arg Leu Gln Asp Ser Trp Glu Asp Ala Ala Ile Leu Leu Ser Asn Thr
            180                 185                 190

Ser Gln Ala Thr Leu Gly Pro Glu His Leu Met Pro Ser Ser Thr Tyr
        195                 200                 205

Val Ala Arg Val Arg Thr Arg Leu Ala Pro Gly Ser Arg Leu Ser Gly
210                 215                 220

Arg Pro Ser Lys Trp Ser Pro Glu Val Cys Trp Asp Ser Gln Pro Gly
225                 230                 235                 240

Asp Glu Ala Gln Pro Gln Asn Leu Glu Cys Phe Phe Asp Gly Ala Ala
                245                 250                 255

Val Leu Ser Cys Ser Trp Glu Val Arg Lys Glu Val Ala Ser Ser Val
            260                 265                 270

Ser Phe Gly Leu Phe Tyr Lys Pro Ser Pro Asp Ala Gly Glu Glu Glu
        275                 280                 285

Cys Ser Pro Val Leu Arg Glu Gly Leu Gly Ser Leu His Thr Arg His
290                 295                 300

His Cys Gln Ile Pro Val Pro Asp Pro Ala Thr His Gly Gln Tyr Ile
305                 310                 315                 320

Val Ser Val Gln Pro Arg Arg Ala Glu Lys His Ile Lys Ser Ser Val
                325                 330                 335
```

-continued

```
Asn Ile Gln Met Ala Pro Pro Ser Leu Gln Val Thr Lys Asp Gly Asp
            340             345             350

Ser Tyr Ser Leu Arg Trp Glu Thr Met Lys Met Arg Tyr Glu His Ile
        355             360             365

Asp His Thr Phe Glu Ile Gln Tyr Arg Lys Asp Thr Ala Thr Trp Lys
    370             375             380

Asp Ser Lys Thr Glu Thr Leu Gln Asn Ala His Ser Met Ala Leu Pro
385             390             395             400

Ala Leu Glu Pro Ser Thr Arg Tyr Trp Ala Arg Val Arg Val Arg Thr
            405             410             415

Ser Arg Thr Gly Tyr Asn Gly Ile Trp Ser Glu Trp Ser Glu Ala Arg
            420             425             430

Ser Trp Asp Thr Glu Ser
            435
```